(12) United States Patent
Hart et al.

(10) Patent No.: US 9,250,248 B2
(45) Date of Patent: Feb. 2, 2016

(54) EARLY DETECTION OF DIABETES

(75) Inventors: Gerald W. Hart, Kingsville, MD (US);
Kyoungsook Park, Severna Park, MD (US); Christopher D. Saudek, Lutherville, MD (US); Zihao Wang, Cary, NC (US)

(73) Assignee: The Johns Hopkins University, Baltimore, MD (US)

( * ) Notice: Subject to any disclaimer, the term of this patent is extended or adjusted under 35 U.S.C. 154(b) by 1083 days.

(21) Appl. No.: 12/445,656

(22) PCT Filed: Oct. 31, 2007

(86) PCT No.: PCT/US2007/083254
§ 371 (c)(1),
(2), (4) Date: Sep. 15, 2010

(87) PCT Pub. No.: WO2008/055242
PCT Pub. Date: May 8, 2008

(65) Prior Publication Data
US 2010/0330594 A1  Dec. 30, 2010

Related U.S. Application Data

(60) Provisional application No. 60/855,981, filed on Nov. 1, 2006.

(51) Int. Cl.
*G01N 33/68* (2006.01)
*G01N 33/66* (2006.01)
*G01N 33/573* (2006.01)
*C07K 16/18* (2006.01)
*C07K 16/40* (2006.01)
*G01N 33/569* (2006.01)

(52) U.S. Cl.
CPC ............ *G01N 33/6893* (2013.01); *C07K 16/18* (2013.01); *C07K 16/40* (2013.01); *G01N 33/56966* (2013.01); *G01N 33/573* (2013.01); *G01N 33/66* (2013.01); *C07K 2317/34* (2013.01); *C07K 2317/41* (2013.01); *G01N 2333/924* (2013.01); *G01N 2400/02* (2013.01); *G01N 2440/38* (2013.01); *G01N 2800/042* (2013.01)

(58) Field of Classification Search
CPC .... C07K 16/18; C07K 16/3061; C07K 16/40; C07K 2317/34; C07K 2317/41; G01N 33/573; G01N 33/56966; G01N 33/6893; G01N 2333/924; G01N 2400/02; G01N 2440/38; G01N 2800/042; G01N 33/66
USPC ........ 435/7.1, 7.21, 7.25, 7.4, 7.5, 7.92, 7.94, 435/7.95, 15, 16; 436/518, 520; 530/388.26, 388.7, 389.1, 389.6, 530/391.1, 391.3
See application file for complete search history.

(56) References Cited

U.S. PATENT DOCUMENTS 7,332,355 B2 * 2/2008 Hsieh-Wilson et al. ...... 436/544

OTHER PUBLICATIONS

Belfiore et al., 1974. Increased beta-N-acetyl-glucosaminidase activity in diabetes mellitus. Clin. Chem. 20: 1229-1230.*
Holt et al., 1987. Erythrocytes contain cytoplasmic glycoproteins: O-linked GlcNAc on band 4.1. J. Biol. Chem 262: 14847-14850.*
Agardh et al., 1991. Association between urinary N-acetyl-beta-glucosaminidase and its isoenzyme patterns and microangiopathy in type 1 Diabetes Mellitus. Clin. Chem. 37: 1696-1699.*
ISR from PCT/US07/083254, filed Oct. 31, 2007.
Akimoto et al., "Elevated Expression of O-G1cNAc-Modified Proteins and O-GlcNAc Transferase in Corneas of Diabetic Goto-Kakizaki Rats", *Investigative Ophthalmology & Visual Science*, 44(9):3802-3809, 2003.
Akimoto et al., "Elevated Post-Translational Modification of Proteins by O-Linked N-Acetylglucosamine in Various Tissues of Diabetic Goto-Kakizaki Rats Accompanied by Diabetic Complications", *Acta Histochem. Cytochem.*, 38(2):131-142, 2005.
Kamemura et al., "Dynamic Interplay between O-Glycosylation and O-Phosphorylation of Nucleocytoplasmic Proteins", *Journal of Biological Chemistry*, 277(21):19229-19235, 2002.
Walgren et al., "High Glucose and Insulin Promote O-GlcNAc Modification of Proteins, Including Alpha-Tubulin", *Am J Physiol Endocrinal Metab*, 284:E424-E434, 2003.
Comer et al., "Characterization of a Mouse Monoclonal Antibody Specific for O-Linked N-Acetylglucosame", *Analytical Biochemistry*, 293:169-177, 2001.
Lehman, et al., "A Single Nucleotide Polymorphism in MGEA5 Encoding O-G1cNAc-selective N—Acetyl-Beta-D Glucosaminidase Is Associated With Type 2 Diabetes in Mexican Americans", *Diabetes*, 54:1214-1221, 2005.
Wells et al., "A Role for N-Acetylglucosamine as a Nutrient Sensor and Mediator of Insulin Resistance", *CMLS, Cell: Mol. Life Sci.*, 60:222-228, 2003.

* cited by examiner

Primary Examiner — Gail R Gabel
Assistant Examiner — James L Grun
(74) Attorney, Agent, or Firm — DLA Piper LLP (US)

(57) ABSTRACT

The present invention is based on the discovery that hexosamine, and in particular the dynamic O-GlcNAcylation of proteins (modification of proteins by the sugar N-acetylglucosamine) both causes insulin-resistance (a hallmark of type II diabetes) and is responsible for glucose toxicity in the disease. Accordingly, the invention provides methods of diagnosing a subject as having or at risk of having pre-diabetes or diabetes. Also provided are methods of characterizing hyperglycemia in a subject, methods of identifying a protein as being associated with hyperglycemia, and kits for detecting pre-diabetes or diabetes.

10 Claims, 13 Drawing Sheets

Band 3 IP (solute carrier family 4, anion exchanger)

* Student's test, $p < 0.001$

EARLY DETECTION OF DIABETES

CROSS REFERENCE TO RELATED APPLICATIONS

This application is a 35 USC §371 National Stage application of International Application No. PCT/US2007/083254 filed Oct. 31, 2007; which claims the benefit under 35 USC §119(e) to U.S. Application Ser. No. 60/855,981 filed Nov. 1, 2006, now abandoned. The disclosure of each of the prior applications is considered part of and is incorporated by reference in the disclosure of this application.

BACKGROUND OF THE INVENTION

1. Field of the Invention

The invention relates generally to hyperglycemia and more specifically to methods of detecting pre-diabetes or diabetes in a subject using O-GlcNAc or an antibody that binds thereto.

2. Background Information

Diabetes is characterized by impaired glucose metabolism manifesting itself among other things by an elevated blood glucose level in the diabetic patient. Underlying defects lead to a classification of diabetes into two major groups. Type 1 diabetes, or insulin dependent diabetes mellitus (IDDM), arises when patients lack insulin-producing beta-cells in their pancreatic glands. Type 2 diabetes, or non-insulin dependent diabetes mellitus (NIDDM), occurs in patients with impaired beta-cell function and alterations in insulin action.

The current treatment for type 1 diabetic patients is injection of insulin, while the majority of type 2 diabetic patients are treated with agents that stimulate beta-cell function or with agents that enhance the tissue sensitivity of the patients towards insulin. The drugs presently used to treat type 2 diabetes include alpha-glucosidase inhibitors, insulin sensitizers, insulin secretagogues, and metformin.

Over time, almost one-half of type 2 diabetic subjects lose their response to these agents. Insulin treatment is instituted after diet, exercise, and oral medications have failed to adequately control blood glucose. The drawbacks of insulin treatment are the need for drug injection, the potential for hypoglycemia, and weight gain.

It has become clear that the development of IDDM is known to occur spontaneously in humans, rats and mice over an indeterminate period of time (months to years). Given that the "pre-diabetic" phase of IDDM is long in duration and clinically asymptomatic, one important opportunity for therapeutic intervention falls during this period. However, effective diagnostic assays that can identify people in this pre-diabetic phase are lacking.

There are major limitations in our current criteria for the diagnosis of diabetes. A Fasting Plasma Glucose (FPG)>125 mg/dl reflects only one aspect of glucose metabolism, which may be stated as the post-absorptive balance of hepatic glucose production and peripheral glucose uptake. It does not reflect the free-living, daily glycemic patterns, the prolonged fasted state or the even post-prandial state. The oral glucose tolerance test (OGTT), in addition to being clinically cumbersome, is also non-physiologic (assuming most meal ingestion does not include 75 gm of concentrated sucrose). Assessing glucose tolerance with the single measure of plasma glucose 2 hours after the oral glucose is therefore crude at best. And as noted, the original basis for defining diabetes was the association of FPG and 2-hour Plasma Glucose (PG), to epidemiologic data on microvascular complications of diabetes, mainly in Pima Indians.

The use of hemoglobin A1c (HbA1c) to diagnose diabetes (in addition to its regular use in following the efficacy of treatment) has long been a controversial issue. While important dissent has been raised, a major problem with assays depending upon non-enzymatic glycation and Amadori chemistry is that they are inherently insensitive and not so useful for detection of pre-diabetics and early-onset diabetes. Thus, the official recommendations have stressed the fact that while quite specific for diabetes, if elevated, HbA1c would be a relatively insensitive way to diagnose early diabetes. Therefore HbA1c has not at this point been accepted as part of the official diagnostic criteria.

The discovery of O-linked β-N-acetylglucosamine (O-GlcNAc) more than 20 years ago disproved the long-held dogma that protein glycosylation is restricted to the luminal compartments of the secretory machinery and to the cell surface and extracellular matrix. Early studies of O-GlcNAc's subcellular localization in rat hepatocytes established that it is highly concentrated at the nuclear envelope, particularly at the nuclear pore complex, but is also abundant and widespread within chromatin. However, several cytosolic and cytoskeletal proteins were also found to be glycosylated with O-GlcNAc (O-GlcNAcylated). Later studies of Drosophila polytene chromosomes established that O-GlcNAcylated proteins are abundant throughout chromosomes. The carboxy-terminal domain of a subpopulation of RNA polymerase II is extensively O-GlcNAcylated, and almost all RNA polymerase II transcription factors are modified by the sugar. So far, more than 500 proteins have been identified to be O-GlcNAcylated, and these proteins are involved in almost all aspects of cellular metabolism.

O-GlcNAcylation not only has an important role in many fundamental cellular processes, but also its dysregulation contributes to the aetiology of important human diseases, particularly diabetes. Accordingly, there exists a need for methods that would enable identification of individuals predisposed to diabetes, and would allow treatment early in the disease process, which may help to avert life-long insulin dependence.

SUMMARY OF THE INVENTION

The present invention is based on the discovery of a correlation between O-GlcNAcylation and diabetes.

The present invention relates to methods of diagnosing a subject as having or at risk of having pre-diabetes or diabetes. In one embodiment, the method includes contacting a test sample from the subject with a reagent that binds to O-linked N-acetyl-glucosamine (O-GlcNAc) to determine a level of O-GlcNAc in the sample, and comparing the determined level of O-GlcNAc to the level of O-GlcNAc in a corresponding normal sample. An increased level of O-GlcNAc in the test sample as compared to the level of O-GlcNAc in the corresponding normal sample is indicative of pre-diabetes or diabetes in the subject. In another embodiment, the reagent is an antibody, and may be detectably labeled. In another embodiment, the invention, further includes contacting the test sample with a naked site antibody that binds to a protein binding site of O-GlcNAc in combination with the O-GlcNAc antibody. Comparing the ratio of bound naked site antibody to bound O-GlcNAc antibody, wherein a ratio less than 1:1, is indicative of pre-diabetes or diabetes in the subject.

In another aspect, the method of diagnosing a subject as having or at risk of having pre-diabetes or diabetes includes detecting an increased level or activity of O-GlcNAcase in a sample from the subject as compared to the level or activity of O-GlcNAcase in a corresponding normal sample. In one embodiment, the detecting includes contacting the sample with an antibody that binds O-GlcNAcase. The antibody can be a monoclonal or polyclonal antibody, and may further be detectably labeled.

In another aspect, the invention provides a method of characterizing hyperglycemia in a subject. In one embodiment, the method includes determining the O-GlcNAcylation level or activity in a sample from the subject and comparing the level to levels of O-GlcNAcylation or activity in corresponding samples from subjects of known gluco-regulatory status. An O-GlcNAcylation level or activity equal to the level of a corresponding sample characterizes the hyperglycemia as being equal to the corresponding sample. In another embodiment, the method further includes determining the level or activity of O-GlcNAc in the test sample and comparing the level or activity of O-GlcNAc in the test sample to the level or activity of O-GlcNAc in the corresponding sample, which confirms the characterization of hyperglycemia in the subject.

In another aspect, the invention provides a method of identifying a protein in a sample as being associated with hyperglycemia. In one embodiment, the method includes contacting the sample with an antibody that binds to O-GlcNAc and detecting binding of the antibody to the O-GlcNAc in the sample. In another embodiment, the antibody can be a monoclonal antibody, and may further be detectably labeled.

In all aspects, the sample may be a blood sample from the subject.

In another aspect, the invention provides a method of monitoring a therapeutic regimen for treating a subject having or at risk of having hyperglycemia. In one embodiment, the method includes determining a change in O-GlcNAcylation level or activity during therapy. In another embodiment, the therapy is insulin treatment.

In another aspect, the invention provides a kit for performing any of the methods of the invention. In one embodiment, the kit includes first container containing an O-GlcNAc binding reagent that binds O-linked N-acetyl-glucosamine (O-GlcNAc) and a second container containing a first detectably labeled reporter. In another embodiment, the kit further includes a third container containing a naked site antibody that binds to a protein binding site of O-GlcNAc. In another embodiment, the kit further includes a second detectably labeled reporter.

DETAILED DESCRIPTION OF THE INVENTION

Figure 1:
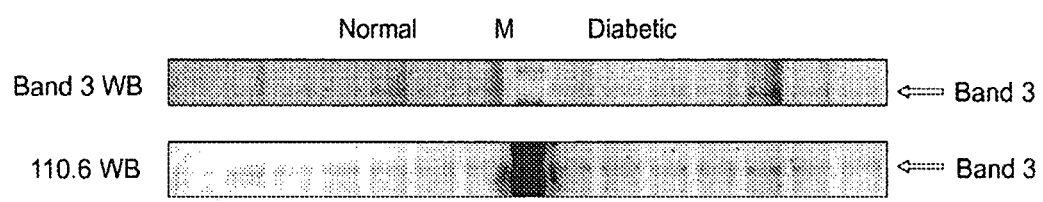
FIG. 1 is a pictorial and graphical diagram showing that O-GlcNAcylation increases in diabetic patients. The results are shown from a total of seven normal and seven diabetic samples.
Figure 1:
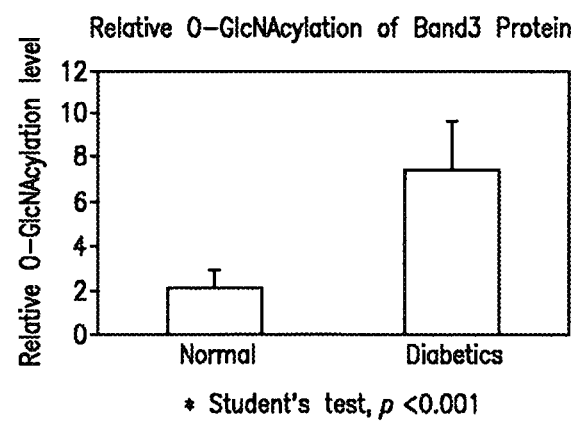

The present invention is based on the discovery of a correlation between O-GlcNAcylation and diabetes.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein "corresponding normal cells" or "corresponding normal sample" refers to cells, or a sample from a subject, that is from the same organ and of the same type as the cells being examined. In one aspect, the corresponding normal cells comprise a sample of cells obtained from a healthy, non-diabetic individual. Such corresponding normal cells can, but need not be, from an individual that is age-matched and/or of the same sex as the individual providing the cells being examined.

As used herein, the terms "sample" and "biological sample" refer to any sample suitable for the methods provided by the present invention. In one embodiment, the biological sample of the present invention is a tissue sample, e.g., a biopsy specimen such as samples from needle biopsy. In other embodiments, the biological sample of the present invention is a sample of bodily fluid, e.g., blood, serum, plasma, urine, and ejaculate.

The dynamic, enzyme catalyzed modification of nucleocytoplasmic proteins by O-linked N-acetylglucosamine (O-GlcNAc) serves as a nutrient sensor to regulate signaling, transcription, proteasomal activity, cytoskeletal assemblies, and cellular responses to stress. It is likely, therefore, that O-GlcNAc can be used to evaluate the gluco-regulatory status of people with subtle as well as overt glucose dysregulation (distinguishing normal, pre-diabetes and diabetes). O-GlcNAcylation is apparently as abundant as phosphorylation in all multi-cellular eukaryotes, often competing with it for the same or adjacent hydroxyl groups on serine or threonine residues. The donor for O-GlcNAcylation, UDP-GlcNAc, occurs within cells at up to millimolar concentrations, levels approaching that for ATP. In fact, between 2% to 5% of all the glucose used by cells is consumed by the hexosamine biosynthetic pathway (HBP), in which UDP-GlcNAc is the major end product.

In one aspect, the invention provides, methods of identifying a protein in a sample as being associated with hyperglycemia. The methods include contacting the sample with a reagent that binds to O-GlcNAc and detecting binding of the reagent to O-GlcNAc. For example, the reagent can be, but is not limited to a polypeptide, a polynucleotide or a small molecule. In one embodiment, the reagent is an antibody. Polynucleotides can be particularly useful as reagents that bind to O-GlcNAc and/or can modulate a specific interaction of molecules because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or anti-sense) and double-stranded polynucleotides. Similarly, the term "peptide" is used broadly herein to refer to a molecule containing two or more amino acids or amino acid analogs (or modified forms thereof) linked by peptide bonds.

The term "antibody" as used in this invention is meant to include intact molecules of polyclonal or monoclonal antibodies, as well as fragments thereof, such as Fab and F(ab')$_2$, Fv and SCA fragments which are capable of binding an epitopic determinant. As such, the term "O-GlcNAc antibody" refers to an antibody that binds to O-GlcNAc. Similarly, the term "naked site antibody" refers to an antibody that binds to a protein binding site of O-GlcNAc. The term "pan-specific antibody" as used herein refers to an antibody that selectively binds at least two members of a group of related polypeptides and does not selectively bind polypeptides outside the group of related polypeptides.

Antibodies are generally produced by immunizing an animal with an antigen, and can be produced by recombinant technology, or by synthesis of the amino acid sequence, for example. Methods of making antibody fragments are known in the art. (See for example, Harlow and Lane, Antibodies: A Laboratory Manual, Cold Spring Harbor Laboratory, New York (1988), incorporated herein by reference). Monoclonal antibodies are made from antigen containing fragments of the protein by methods well known to those skilled in the art (Kohler & Milstein, *Nature* 256:495 (1975); Coligan et al., sections 2.5.1-2.6.7; and Harlow et al., *Antibodies: A Laboratory Manual*, page 726 (Cold Spring Harbor Pub. 1988), which are hereby incorporated by reference. Briefly, monoclonal antibodies can be obtained for example, by injecting mice with a composition comprising an antigen/ligand, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., "Purification of Immunoglobulin G (IgG)" in *Methods In Molecular Biology*, Vol. 10, pages 79-104 (Humana Press 1992).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated herein by reference).

Antibodies that bind to an invention polypeptide can be prepared using an intact polypeptide or fragments containing small peptides of interest as the immunizing antigen. For example, it may be desirable to produce antibodies that specifically bind to the amino- or carboxyl-terminal domains of an invention polypeptide. For the preparation of polyclonal antibodies, the polypeptide or peptide used to immunize an animal is derived from translated cDNA or chemically synthesized and can be conjugated to a carrier protein, if desired. Commonly used carrier proteins which may be chemically coupled to the immunizing peptide include keyhole limpet hemocyanin (KLH), thyroglobulin, bovine serum albumin (BSA), tetanus toxoid, and the like.

The antibodies of the invention can be bound to many different carriers and used to detect the presence of an antigen comprising the polypeptides of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

As used herein, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

As used herein, the term "pre-diabetes" refers to either impaired glucose tolerance (IGT) or impaired fasting glucose (IFT), in order to simplify the public message of early glucose intolerance. IGT typically refers to a condition in which the blood sugar of a subject is elevated between 140 and 199 mg/dL after a two-hour glucose challenge. IFT typically refers to a condition in which the fasting blood sugar is elevated between 110 and 125 mg/dL after an overnight fast but is not high enough to be true diabetes.

O-GlcNAcylation is in many ways distinct from 'classical' protein glycosylation. First, it is found mostly within the cytoplasm or nucleoplasm. Second, unlike the extraordinarily complex array of glycans found on extracellular glycoproteins, O-GlcNAc is not elongated or further modified. Third, O-GlcNAc cycles by means of mechanisms and on a timescale similar to those of phosphorylation and quite different from the cycling of complex extracellular glycans. Recent studies have shown that the HBP, and O-GlcNAc, in particular, play a key role in insulin-resistance and in glucose toxicity. Elevating O-GlcNAc in adipocytes blocks insulin signaling, preventing both glucose uptake and the activation of glycogen synthase. Targeted over-expression of O-GlcNAc transferase (OGT) to muscle or adipose tissue in mice causes overt diabetes.

It is also now clear that many of the toxic effects of glucose require its conversion into glucosamine. McClain and Crook have elegantly summarized the current understanding of the roles of hexosamines and insulin-resistance (McClain, et al., (1996) Hexosamines and Insulin Resistance *Diabetes* 45, 1003-1009). Importantly, glucosamine (GleN) enters cells via the glucose transporters but has a $K_m$ about three-times as that for glucose and a similarly low affinity for hexokinase. Therefore, without being limited to theory, it is likely that the effects of GlcN are not due to competition for glucose uptake or metabolism. The first studies to directly link GlcN metabolism with the toxicity of glucose in diabetes were carried-out by Marshall, et al. (Marshall, et al., (1991) Discovery of a Metabolic Pathway Mediating Glucose-induced Desensitization of the Glucose Transport System. Role of Hexosamine Biosynthesis in the Induction of Insulin Resistance *J. Biol. Chem.* 266(8), 4706-4712; Traxinger, R. R., and Marshall, S. (1989) Role of Amino Acids in Modulating Glucose-induced Desensitization of the Glucose Transport System. *J. Biol. Chem.* 264, 20910-20916). The key observations were the findings that GleN is many times more potent than Glc in inducing insulin-resistance in cultured adipocytes, that glucose's ability to induce insulin resistance could be blocked by deoxynorleucine (DON), a drug that inhibits the glucose-fructose-6-phosphate amidotransferase (GFAT), the enzyme that converts fructose-6-P to glucosamine-6-P, and that this blockage could be by-passed by adding GleN to the culture media. Later studies have strengthened the hypothesis that GlcN flux is key to transcriptional regulation of a number of genes important to glucose homeostasis.

Rossetti et al. tested whether increased flux through the hexosamine pathway induced insulin-resistance in vivo in rats (Rossetti, et al., (1995) In vivo glucosamine infusion induces insulin resistance in normoglycemic but not in hyperglycemic conscious rats *J. Clin. Invest.* 96, 132-140). They found that increased GlcN availability induced severe skeletal muscle insulin resistance in normal rats. In later studies, Rossetti and colleagues also showed that GleN metabolism also plays a role in fat-induced insulin resistance in vivo (Hawkins, et al., (1997) Role of the Glucosamine Pathway in Fat-induced Insulin Resistance *J. Clin. Invest.* 99 (9), 2173-2182). In clamp studies in rats they demonstrated that elevated free fatty acids concomitantly increased UDP-GlcNAc levels by two-fold in muscle. Using three independent methods of increasing UDP-GlcNAc levels about two-fold in muscle, they showed that this apparently modest increase indeed induced insulin resistance. They proposed that elevated fatty acids, like hyperglycemia, induce insulin resistance by increasing production of glucosamine metabolites. In in vivo studies in the rat, Rossetti and colleagues co-infused uridine with GlcN and concomitantly prevented any changes in the UDP-Glc levels in skeletal muscle (Hawkins, et al., (1997) The tissue concentration of UDP-N-acetyl-glucosamine modulates the stimulatory effect of insulin on skeletal muscle glucose uptake *The Journal Biological Chemistry* 272(8), 4889-4895) to show that induction of insulin resistance depended upon the levels of UDP-GlcNAc, not on UDP-Glucose. These workers also showed a one-hundred fold increase in the rate of incorporation of labeled GlcN into Glut4 transport vesicles under conditions of insulin resistance and concluded there was an increase in the glycosylation of glycoproteins associated with Glut4 containing vesicles.

The levels of O-GlcNAc on nucleocytoplasmic proteins are highly sensitive to the concentrations of glucose and other nutrients surrounding cells, and to nearly all types of cellular stress. The extent, and indeed the specificity, of O-GlcNAc addition to proteins by OGT is highly responsive to UDP-GlcNAc over an astonishingly broad range of concentrations (e.g., nanomolar to over 100 mM). O-GlcNAc cycles on a time scale similar to phosphorylation, but does so at different rates, at different attachment sites on the same protein, and it also cycles at widely different rates on different proteins.

Accordingly, the present invention provides methods of detecting differential changes in the O-GlcNAc levels on a few key blood proteins to monitor the history of cellular exposure to changes in nutrients, especially glucose, and to oxidative stress. Since O-GlcNAc on some proteins turns over rapidly and on others cycles more slowly, the invention provides, by comparative quantitative analyses, the ability to estimate both the severity and duration of glucose dysregulation in individuals by monitoring the levels of O-GlcNAc simultaneously on several key proteins in blood.

However, since O-GlcNAc is uncharged and small, it does not usually alter the migration of proteins in gel electrophoresis, even on high-resolution two-dimensional gels. Further, all cells contain high concentrations of hydrolases that rapidly remove O-GlcNAc from intracellular proteins upon cellular damage. Like phosphorylation, O-GlcNAcylation is often substoichiometric at any site on a protein, making it particularly difficult to detect by physical methods, such as mass spectrometry. Most importantly, O-GlcNAc is very labile upon ionization in a mass spectrometer, and much of it is often lost at the source. O-GlcNAc is also almost entirely lost during standard CAD (collision-activated dissociation) methods. In MALDI-MS (matrix assisted laser-desorption/ionization mass spectrometry) the unmodified peptides are preferentially ionized, often completely suppressing the signal from O-GlcNAc-peptide ions (which are less surface active), when both are present in a mixture. Fortunately, recently developed potent hexosaminidase inhibitors and pan specific O-GlcNAc antibodies have greatly improved the ease of detection of O-GlcNAc. Furthermore, when new mass-spectrometric methods—such as FTMS-ECD (Fourier transform mass spectrometry with electron-capture dissociation) or ETD (ion-trap mass spectrometry with electron-transfer dissociation)—have been combined with newly developed enzymatic/chemical tagging and enrichment methods, they have facilitated detection and site mapping of O-GlcNAc. Finally, analyses of O-GlcNAc function are complicated by the lack of a recognizable consensus motif.

Thus, in one aspect, the invention provides a method of diagnosing a subject as having or at risk of having pre-diabetes or diabetes. The method includes contacting a test sample from the subject with a reagent that binds to O-linked N-acetyl-glucosamine (O-GlcNAc) to determine a level of O-GlcNAc in the sample, and comparing the determined level of O-GlcNAc to the level of O-GlcNAc in a corresponding normal sample. An increased level of O-GlcNAc in the test sample as compared to the level of O-GlcNAc in the corresponding normal sample is indicative of pre-diabetes or diabetes in the subject. The method may further include contacting the test sample with a reagent that binds to the protein binding site of O-GlcNAc (e.g., a naked site antibody) in combination with the reagent that binds to O-GlcNAc, and comparing the ratio of bound naked site reagent to bound O-GlcNAc reagent. A ratio less than 1:1 is indicative of pre-diabetes or diabetes in the subject.

Due to the lability of O-GlcNAc a method to both map sites and identify O-GlcNAcylated proteins was developed. At first, loss of water (−18 m/z) upon alkali-induced β-elimination of cytomegaloviral O-GlcNAcylated proteins was used to map sites. Recently, a modified β-elimination/Michael addition (BEMAD) method used for site mapping O-phosphate was used to develop a similar method that tags O-GlcNAc with dithiothreitol (DTT).

BEMAD has proven highly useful for simultaneously mapping sites and identifying O-GlcNAc modified proteins. The thiol-enrichment step allows only the modified tryptic peptides to be analyzed by LC-MS/MS, greatly simplifying analyses. It is also possible to examine both phosphate and O-GlcNAc simultaneously, either by taking advantage of the 10- to 100-fold higher sensitivity of O-GlcNAc to β-elimination or by splitting the sample and treating the peptides with O-GlcNAcase and alkaline phosphatase. Density labeling with deuterated DTT has allowed for semi-quantitative proteomics.

O-G1cNAcylation is abundant on proteins involved in stress responses and energy metabolism. So far, approximately 50 sites of O-GlcNAc addition have been mapped. These have revealed that there is no obvious consensus sequence. However, about 50% of the known sites have a Pro-Val-Ser motif similar to that recognized by proline-directed kinases. Many of the known O-GlcNAc sites have high 'PEST' scores—PEST (Pro-Glu-Ser-Thr (SEQ ID NO:43)) being a sequence that is associated with rapid degradation—which suggests that O-GlceNAcylation at these sites might slow or prevent degradation (Rechsteiner, et al., PEST sequences and regulation by proteolysis. *Trends Biochem. Sci.* 21, 267-271 (1996)).

Nucleocytoplasmic β-N-acetylglucosaminidase (O-GlcNAcase) was first identified as 'hexosaminidase C' (Braidman, I. et al. Characterisation of human N-acetyl-beta-hexosaminidase C. *FEBS Lett.* 41, 181-184 (1974)). O-GlcNAcase was purified from the rat kidney and bovine brain, and the human gene was cloned using peptide sequencing (Gao, et al., Dynamic O-glycosylation of nuclear and cytosolic proteins: cloning and characterization of a neutral, cytosolic β-Nacetylglucosaminidase from human brain. *J. Biol. Chem.* 276, 9838-9845 (2001)). The cloned sequence was found to be identical to that of MGEA5 (meningioma-expressed antigen 5) (Heckel, et al. Novel immunogenic antigen homologous to hyaluronidase in meningioma. *Hum. Mol. Genet.* 7, 1859-1872 (1998)), which had been identified genetically in human meningiomas. MGEA5 maps to a chromosomal region associated with late-onset Alzheimer's disease in humans (10q24.1). O-GlcNAcase seems to be a bifunctional enzyme. The N terminus encodes the glycosidase domain, whereas the C terminus shows homology to the GCN5 histone acetyltransferases (HATs). O-GlcNAcase is reported to have both HAT and O-GlcNAcase activities in vitro (Toleman, et al., Characterization of the histone acetyltransferase (HAT) domain of a bifunctional protein with activable OGlcNAcase and HAT activities. *J. Biol. Chem.* 279, 53665-53673 (2004)). In vitro, caspase-3 cleaves O-GlcNAcase to separate the HAT and O-GlcNAcase domains, and the latter domain remains catalytically active (Wells, et al. Dynamic O-glycosylation of nuclear and cytosolic proteins: further characterization of the nucleocytoplasmic β-N-acetylglucosaminidase, O-GlcNAcase. *J. Biol. Chem.* 277, 1755-1761 (2002)). O-GlcNAcase also interacts with a vast number of cellular proteins, but the location of interaction sites on the enzyme and the functional significance of these interactions have not yet been determined. O-GlcNAcase and uridine diphospho-N-acetylglucosamine:polypeptide β-N-acetylglucosaminyltransferase (OGT), which catalyses the addition of O-GlcNAc, sometimes occur within the same functional complex. In these complexes, both enzymes must be tightly regulated to prevent futile cycling of O-GlcNAc.

Thus, in another aspect, the invention provides a method of diagnosing a subject as having or at risk of having pre-diabetes or diabetes. The method includes detecting an increased level or activity of O-GlcNAcase in a sample from the subject as compared to the level or activity of O-GlcNAcase in a corresponding normal sample.

Recent studies have shown that O-GlcNAc has a key role in the regulation of insulin signaling and as a mediator of glucose toxicity (Wells, et al., A role for N-acetylglucosamine as a nutrient sensor and mediator of insulin resistance. *Cell. Mol. Life Sci.* 60, 222-228 (2003); and Buse, Hexosamines, insulin resistance, and the complications of diabetes: current status. *Am. J. Physiol. Endocrinol. Metab.* 290, E1-E8 (2006)). Increasing O-GlcNAcylation in adipocytes or muscle blocks insulin signalling at several points. Elevated O-GlcNAcylation on insulin receptor substrate seems to reduce its interactions with phosphatidylinositol-3-OH kinase, thus blocking insulin signalling at an early stage (Vosseller, et al., Elevated nucleocytoplasmic glycosylation by O-GlcNAc results in insulin resistance associated with defects in Akt activation in 3T3-L1 adipocytes. *Proc. Natl Acad. Sci. USA* 99, 5313-5318 (2002); and Federici, et al., Insulin-dependent activation of endothelial nitric oxide synthase is impaired by O-linked glycosylation modification of signaling proteins in human coronary endothelial cells. *Circulation* 106, 466-472 (2002)). In transgenic mouse models, OGT overexpression in muscle or adipose tissue causes overt diabetes (McClain, et al. Altered glycan-dependent signaling induces insulin resistance and hyperleptinemia. *Proc. Natl. Acad. Sci. USA* 99, 10695-10699 (2002)). Many aspects of 'glucose toxicity' require its metabolism into glucosamine, which, in turn, elevates UDP-GlcNAc and increases O-GlcNAcylation. Hyperglycaemia, hyperlipidaemia and/or hyperinsulinaemia all result in abnormal increases in O-GlcNAcylation, which disturbs the normal dynamic balance between O-GlcNAcylation and O-phosphorylation that controls signaling, transcription and other cellular functions. It is proposed that, when prolonged, this imbalance contributes to the chronic and pleiotropic toxicity associated with diabetes.

In cultured adipocytes, glucosamine is much more potent than glucose in inducing insulin-resistance. Glucose's ability to induce insulin resistance is prevented by deoxynorleucine (DON), an inhibitor of glucose:fructose amidotransferase (GFAT), the key enzyme that converts fructose-6-phosphate to glucosamine-6-phosphate (McClain, et al. Altered glycan-dependent signaling induces insulin resistance and hyperleptinemia. *Proc. Natl. Acad. Sci. USA* 99, 10695-10699 (2002)). Many later studies led to the current models for the roles of both hexosamine metabolism and O-GlcNAc in the aetiology of diabetes. Glucosamine metabolism is required for fat-induced insulin resistance in vivo. O-GlcNAcylation of glycogen synthase reduces its activation by insulin (Parker, et al., Hyperglycemia and inhibition of glycogen synthase in streptozotocin-treated mice: role of O-linked N-acetylglucosamine. *J. Biol. Chem.* 279, 20636-20642 (2004)). A single-nucleotide polymorphism commonly occurs in the MGEA5 gene (which encodes O-GlcNAcase) within a human population with type 2 diabetes (Lehman, et al., A single nucleotide polymorphism in MGEA5 encoding O-GlcNAcselective N-acetyl-beta-d glucosaminidase is associated with type 2 diabetes in Mexican Americans. *Diabetes* 54, 1214-1221 (2005)). In rat skeletal muscle, hyperinsulinaemia, as seen in type 2 diabetes, markedly increases the levels of O-GlcNAc on many proteins (Yki-Jarvinen, et al., Insulin and glucosamine infusions increase O-linked N-acetyl-glucosamine in skeletal muscle proteins in vivo. *Metabolism* 47, 449-455 (1998)).

Elevated glucose levels increase the O-GlcNAcylation of proteins in the insulin secreting pancreatic β-cells (Liu, et al., Glucose stimulates protein modification by O-linked GlcNAc in pancreatic β cells: linkage of O-linked GlcNAc to β cell death. *Proc. Natl. Acad. Sci. USA* 97, 2820-2825 (2000)). Hyperglycaemia qualitatively and quantitatively alters the expression of many O-GlcNAcylated proteins in rat aorta and in cultured rat aortic smooth muscle, suggesting a role for O-GlcNAc in glucose toxicity to vascular tissues (Wells, et al., A role for N-acetylglucosamine as a nutrient sensor and mediator of insulin resistance. *Cell. Mol. Life Sci.* 60, 222-228 (2003); and Buse, Hexosamines, insulin resistance, and the complications of diabetes: current status. *Am. J. Physiol. Endocrinol. Metab.* 290, E1-e8 (2006)). Transgenic mice overexpressing the glucose transporter protein GLUT1 in muscle are insulin resistant and have increased O-GlcNAcylation of GLUT4 vesicle-associated proteins (Buse, 2006). Non-esterified fatty acids increase both UDPGlcNAc levels and the O-GlcNAc-dependent DNA-binding activity of the SP1 transcription factor in cultured human myotubes (see Buse, 2006). Cultured myotubes grown in high glucose and/or insulin have enhanced O-GlcNAcylation of numerous proteins (Wells, et al., 2003; Buse, 2006; and Yki-Jarvinen, et al., 1998). Glycoproteomic analyses of these myotubes show that hyper-O-GlcNAcylated proteins include HSP70, α-tubulin and SP1 (Walgren, et al., High glucose and insulin promote O-GlcNAc modification of proteins, including α-tubulin. *Am. J. Physiol. Endocrinol. Metab.* 284, E424-E434 (2003)). Rat myocytes exposed to high glucose levels exhibit altered O-GlcNAcylation, which contributes to impaired calcium cycling in the heart and to diabetic cardiomyopathy by reducing the transcription of a sarcoplasmic reticulum calcium ATPase, SERCA2a (Clark, et al., Diabetes and the accompanying hyperglycemia impairs cardiomyocyte calcium cycling through increased nuclear O-GlcNAcylation. *J. Biol. Chem.* 278, 44230-44237 (2003)). When diabetic cardiomyocytes are transfected with an adenovirus encoding O-GlcNAcase, cardiomyocyte functions improve markedly.

Other recent studies have specifically addressed the interpretation and limits of hemoglobin A1c (HbA1c) and of the oral glucose tolerance test (OGTT). Derr et al. showed that HbA1c, as used clinically, does not significantly reflect the variance of glycemia, but only the mean (Derr, et al., (2003) Is Hemoglobin A1c Affected by Glycemic Instability? *Diabetes Care* 26, 2728-2733). HbA1c and self-monitoring data were analyzed from 256 individuals with diabetes, over a very wide range of glycemic control and lability.

From these data, lability of glycemia was found not to contribute significantly to HbA1c. The report was clinically important in establishing the interpretation of HbA1c. It also suggested the limitations of the HbA1c assay in that lability of glycemia, not reflected in HbA1c, is a crucial factor in diabetic management, particularly in avoiding clinical hypoglycemia. Thus, it is now clear that hyperglycaemia, hyperlipidaemia and insulin all regulate O-GlcNAcylation, which, in turn, modulates signaling and transcription. Evidence is mounting that dysregulation of O-GlcNAcylation is a major mechanism underlying the molecular basis of glucose toxicity and insulin resistance, the two main hallmarks of type 2 diabetes.

However, the extent of O-GlcNAcylation of cellular proteins is highly sensitive to nutrients and stress, particularly oxidative stress. Accordingly, in one embodiment, the invention provides a method of identifying O-GlcNAcylated proteins in a sample (e.g., human red blood cells) from a subject whose site-specific O-GlcNAcylation could be quantified in order to detect pre-diabetic or diabetic patients, and that these findings would serve as a basis for the development of a simple immuno-assay that could be used to screen a large patient population.

In another aspect, the invention provides methods for characterizing hyperglycemia in a subject. The method includes determining the O-GlcNAcylation level or activity in a sample from the subject and comparing the level to levels of O-GlcNAcylation or activity in corresponding samples from subjects of known gluco-regulatory status. A O-GlcNAcylation level or activity equal to the level of a corresponding sample characterizes the hyperglycemia as being equal to the corresponding sample. The method may further include determining the level or activity of O-GlcNAc in the test sample and comparing the level or activity of O-GlcNAc in the test sample to the level or activity of O-GlcNAc in the corresponding sample in order to confirm the characterization of hyperglycemia in the subject. Exemplary characterizations of hyperglycemia include, but are not limited to, pre-diabetes, Mild Type 2 Diabetes, Uncontrolled Type 2 Diabetes, Well Controlled type 1 diabetes, and Uncontrolled type 1 diabetes.

The characterizations may be made as follows. (1) "Pre-Diabetes": People who, with OGTT, have either IFG (FPG 100-125 mg/dl) or IGT (2-hour PG 140-199 mg/dl), and no previous diagnosis of diabetes. (2) "Mild Type 2 Diabetes": Meeting clinical criteria for type 2 diabetes of at least 2 years' duration, these people will have HbA1c <7% and FPG <140 mg/dl on diet and exercise therapy alone. With mild type 2 diabetes, the standard deviation (SD) of their SMBG results will be <30 mg/dl. (3) "Uncontrolled Type 2 Diabetes": As for Mild Type 2 Diabetes, except that they will have HbA1c >9% and FPG >200 mg/dl, treated with exogenous insulin. These subjects will have (since they have type 2 diabetes) relatively stable glycemia, with SD <50 mg/dl on SMBG, but in poor control. (4) "Well Controlled Type 1 Diabetes": Again, with clinical criteria for type 1 diabetes, and HbA1c <7%, these subjects will be similar to those of group 2 in terms of mean glycemia, but the important difference is that, having type 1 diabetes, they will have much more labile glycemia (SD >70 mg/dl). (5) "Uncontrolled Type 1 Diabetes": HbA1c >9%, could be similar to group 4. except, again, for their relatively extreme lability of glycemia (SD >90 mg/dl).

Using samples obtained from the Johns Hopkins diabetes center, in conjunction with glycomics, over 30 O-GlcNAcylated proteins were identified from human erythrocytes. It was further observed that the O-GlcNAcylation state of those proteins is indeed reflective of the diabetic status of the subjects from which the samples were obtained. During these studies, it was found that the enzyme that removes O-GlcNAc from proteins, O-GlcNAcase, is also strikingly increased in red blood cells from patients with diabetes. Early site-specific OGlcNAcylation analyses support the concept that increases in O-GlcNAc, due to diabetes, are even more pronounced at the individual site level.

As such, once disease is established and a treatment protocol is initiated, the methods of the invention may be repeated on a regular basis to monitor the level of hyperglycemia or diabetes in the subject. The results obtained from successive assays may be used to show the efficacy of treatment over a period ranging from several days to months. Accordingly, the invention is also directed to methods for monitoring a therapeutic regimen (e.g., insulin treatment) for treating a subject having pre-diabetes or diabetes. A comparison of the level of O-GlcNAcylation prior to and during therapy indicates the efficacy of the therapy. Therefore, one skilled in the art will be able to recognize and adjust the therapeutic approach as needed.

In another aspect, the invention provides kits for detecting pre-diabetes or diabetes in a subject that include a first container containing an O-GlcNAc binding reagent that binds O-GlcNAc, and a second container containing a first detectably labeled reporter. In one embodiment, the kit includes instructions for practicing the methods of the invention. In another embodiment, the kit further includes a third container containing a naked site antibody that binds to a protein binding site of O-GlcNAc. In another embodiment, the kit further includes a second detectably labeled reporter.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Quantification of Extent and Duration of Hyperglycemia

This example will demonstrate the use of the streptozotocin (STZ)-treated rat model to precisely quantify the relationship between the extent and duration of hyperglycmia and changes in O-GlcNAc on proteins in blood cells and plasma.

The STZ-treated rat model provides a powerful tool for inducing hyperglycemia and evaluating the effects of the duration and extent of the changes on concomitant changes in O-GlcNAcylation. In clinical diabetes, the main metabolic and long-term pathologic effects of diabetes are of course seen regardless of the etiology of the diabetes. These initial studies will allow us to further develop the proteomic O-GlcNAc methods for blood cells and plasma, to precisely quantify the relationship between O-GlcNAc and glucose concentrations in blood. Further, they will allow careful comparisons of observed O-GlcNAc changes to concomitant changes in glycated hemoglobin (HbA1c) and to fructosamine (glycated serum proteins). Finally, these animal studies will provide a gauge of the limitations of detection and signal-to-noise prior to working with the less controllable human samples.

In individual experiments, five male Sprague-Dawley Rats (~400 g) will be used in each experimental and control group. Rats will be purchased and allowed to stabilize in animal facilities for at least 2 days. Blood will be collected from all rats by tail vein using a tuberculin syringe (~250-500 microliters) into screw cap tubes containing sodium citrate (~0.105M final concentration) to prevent clotting and inhibit glycolysis, immediately placed on ice. Blood will be centrifuged at 1,500 g and plasma removed to a clean tube and centrifuged a second time to remove any cellular debris, and the top 90% removed to a clean tube. Cell pellets will be washed via centrifugation (1,500 g) two times with isotonic saline. Plasma and blood cells (resuspended in isotonic saline, 10% DMSO) will be stored at −70° C. until analyzed.

Streptozotocin (STZ; 70 mg/Kg body weight) dissolved in sterile citric acid-trisodium citrate (0.1 mmol/L) pH 4.5 will be injected i.p. into 5 rats; 5 control rats will receive an equal volume of buffer alone. Blood will be collected on days 1, 3, 5, 7, 9, 14, 21, 28, 35, and 42, and rats will be sacrificed by rendering them unconscious with carbon dioxide gas from a cylinder within an enclosed chamber and then by decapitation using a rat guillotine. At the conclusion of every experiment, animals will be bled-out, and tissues will be snap frozen (−70° C.), and saved for later global analyses of O-GlcNAc levels. Any changes seen in blood cells will be correlated to concomitant changes seen at the end-points in key tissues (e.g., skeletal muscle cardiac muscle, adipose, liver, pancreas, brain, retina).

Literature and experience has shown that the STZ-treated rats will have blood glucose levels of approximately 20-40 mmol/L within a week of STZ treatment. Effects of both short term and longer term hyperglycemia on O-GlcNAcylation will be examined. Blood samples will then be assayed for glucose, HbA1c, "fructosamine", and modification of specific blood proteins by O-GlcNAc, as described below. These initial animal studies will need to be independently repeated at least three times to provide an indication of quantitative reproducibility. Multiple proteomic analyses will also be performed on each sample to allow statistical evaluation of reproducibility.

Changes in O-GlcNAc—If STZ-rats are treated with insulin around week 7 after treatment with STZ, their glucose levels can be restored to normal or even lower. Using various concentrations of insulin, changes in O-GlcNAc in blood can thus be monitored as the animals go from prolonged or short-term high glucose to normal or low glucose. Thus, the STZ-rat model allows for the comparison of the down side of the curve, as well as the up side, in a highly controlled manner with controlled genetic background and epigenetic factors not possible with humans.

Animals will be treated with STZ, as above. However, after about day 7, insulin (0 to about 12 U/kg/day) will be administered by subcutaneous implants of bovine insulin. These implants (Linplant, Scarborough, Ontario), which use palmitic acid as the vehicle, are introduced under the dorsal skin of rats that are lightly anaesthetized with Ketolar (30 mg/kg, i.p.). Full size implants release ~2 U/day. The amount of insulin released can be controlled by cutting the implants to various sizes, making it possible to produce intermediate levels of hyper- or hypoglycemia. Controls will receive identical implants with vehicle only. Blood will be collected, fractionated and stored, as described above. Five animals will be used in each group and the experiment repeated at least three times. Multiple (at least three) analytical and proteomic analyses will be performed in each sample to allow for statistical analyses of data. At the conclusion of every experiment (as described above), animals will be bled-out, and tissues will be saved for later global proteomic analyses of O-GlcNAc levels.

Measurement of glucose levels, Hemoglobin A1c and "Fructosamine" in Blood—Glucose levels will initially be measured using a OneTouch Ultra Blood glucose monitoring system (Lifescan, Mountain View, Calif.). Glucose will also be determined using a more accurate hexo-kinase/glucose-6-phosphate dehydrogenase (G-6-PDH) coupled enzyme assay kit (Sigma) that measures absorbance at 340 nm to quantify production of NADH. Hemoglobin A1c (HbA1c) will be determined by the use of the Micromat II Hemoglobin A1c Instrument (BioRad Laboratories, Hercules, Calif.). Glycated hemoglobins will also independently be quantified by either capillary electrophoresis (ion-pair method) or by cation-exchange HPLC.

"Fructosamine" (mostly glycated serum albumin), which putatively reflects glucose-control over a shorter time-period than HbA1c will be determined by the Diazyme enzyme assay (Diazyme labs., San Diego, Calif.), which uses Proteinase K to digest glycated serum proteins and a "fructosaminase" that catalyzes the oxidative degradation of Amadori glycated protein fragments to produce amino acids, glucosone and hydrogen peroxide. The hydrogen peroxide produced is subsequently detected colorimetrically. Alternatively, a more standard colorimetric assay based upon the ability of ketoamines to reduce nitroblue tetrazolium to formazan will be used. All of the above assays will be carried-out on each sample a sufficient number of times to evaluate statistical significance. Means, std deviations and Pearson correlation coefficients will be calculated.

EXAMPLE 2

Quantitative Proteomic Analysis of O-GlcNAc Modified Proteins

This example demonstrates the quantitative proteomic analyses of O-GlcNAc modified proteins using antibodies, and a lectin (sWGA) to O-GlcNAc, in conjunction with DIGE 2D gel electrophoresis, BEMAD density labeling and MS/MS to identify proteins, sites and quantify changes.

DIGE—2-D Fluorescence Difference Gel Electrophoresis (DIGE) protocols will be designed to differentially label the control and experimental samples, affinity purify the O-GlcNAc proteins using a pan-specific O-GlcNAc monoclonal antibody, measure differences using 2D DIGE, and identify spots with MS/MS. The experimental design for the DIGE 2D gel proteomic experiments is modified from published methods. For most studies, a saturation labeling method, in which Cy3 and Cy5 fluorescent dyes have a maleimide group that is selectively reactive with cysteine via its thiol residue (Amersham). The advantage of this approach is several fold: 1) Cysteine is much less abundant than lysine residues allowing quantitative labeling of proteins and thus higher sensitivity than the original DIGE method, which only labels ~5% of the proteins. 2) The saturation labeling improves accuracy of spot-picking for MS/MS. Studies have shown that in the original DIGE method as much as 40% of the proteins could not be selected accurately by automated spot picking. 3) Attaching the dye to the cysteine residues does not block tryptic cleavage of the proteins.

Typically, 50 µl of plasma will be thawed and mixed with an equal volume RIPA buffer (1% Nonidet P-40, 0.5% deoxycholate, 0.1% SDS in TBS (15 mM Tris/HCl, pH 7.5, 150 mM NaCl). Cell pellets will solubilized in RIPA buffer and centrifuged at 10,000 g to remove unsolubilized material. Protein concentration in samples will be determined by a dot blot assay, which is not interfered with by heme or detergents. Samples will then be reduced with 1 mM Tris-(2-carboxyethyl)phosphine (TCEP). Cy dyes (10 mM in dimethylformamide) will be added to samples at a ratio of 20 nmol dye/50 µg protein. Samples will be vortexed and incubated for 37° C. for 30 min.

Reactions will be quenched by diluting 5× with RIPA buffer. Samples will then be centrifuged at 10,000 g and supernatants removed to a clean tube in order to remove any insolubles generated during the reaction. Control samples will be labeled with Cy3 (monoisotopic mass=672.2982; Ex=~540; Em=590) and experimental samples with Cy5 (monoisotopic mass=684.2981 Ex=625; Em=680). If preliminary studies show it is necessary, a potent O-GlcNAcase inhibitor will be added to the labeling buffer (10 uM O-(2-acetamido-2-deoxy-D-glucopyranosyli-dene)-amino-N-phenylcarbamate; Ki=53 nM; PUGNAC). Equal volumes of control (Cy3 tagged) and experimental (Cy5 tagged) will then be mixed for immunoaffinity purification of O-GlcNAc modified proteins.

Immunopurification using anti-O-GlcNAc monoclonal antibody. Cy-tagged supernatant samples will first be pre-cleared for 1 h at 4° C. with anti-IgM-agarose. Samples will then be batch bound overnight at 4° C. with the O-GlcNAc-specific antibody 110.6 (~1 mg/ml resin) covalently coupled with dimethyl pimelimidate to anti-IgM-agarose. Preliminary experiments using 1D gels and Western blotting with anti-O-GlcNAc will be used to determine the size of the column. The affinity columns will be washed five times with 10 column volumes of RIPA (1% Nonidet P-40, 0.5% deoxycholate, 0.1% SDS in TBS (15 mM Tris/HCl, pH 7.5, 150 mM NaCl)), 5 column volumes of TBS containing 4% CHAPS, and then eluted with 1 M GlcNAc in the TBS/CHAPS buffer. GlcNAc eluted samples will then be concentrated with buffer exchange using spin columns (10 kDa cutoff) into the isoelectric focusing buffer: (4M urea, 2M thiourea, 2% CHAPS, 2% sulphobetaines 3-10, 0.5% triton ×100, 0.8% Pharmalytes 3-10, and 4 mg/ml Dithiothreitol (DTT)).

Isoelectric Focusing—Large 2D gels will be ran using a Multiphor II (Amersham) and gel apparatus. The 24 cm Isoelectric Focusing Strips have a maximum protein load ~200

μg. Typically samples of ~1500 μl in focusing buffer (above) are used in rehydrating strips which are subjected to isoelectric focusing (IEF).

Second Dimension SDS-PAGE~Strips are placed into 15 ml conical tubes with freshly made equilibration solution (50 mM Tris-HCl pH8.8, 6M urea, 30% glycerol, 2% SDS) and gently rocked for 15 min in the dark. Strips are loaded with the acidic end next to the molecular weight marker well and seal with 1% agarose solution. Cy2 labeled markers (~7.5 μg) are applied to the molecular weight marker well. After electrophoresis the gels are rinsed three times with milli-Q water are ready to be scanned using a Typhoon laser scanner. Control and experimental samples will be quantified by DeCyder differential In-gel analysis (DIA) software. Gel to gel matching of standard spot maps from each gel will be followed by statistical analysis of protein abundance change between samples using the DeCyder BVA (Biological Variation Analysis) software module. In this system, since each sample spot is co-detected with a standard spot map, all spots are compared internally to the same pooled standard.

Protein Extraction—Proteins that appear to be differently O-GlcNAcylated between control and experimental samples will be cut out of the gel using an automated spot cutter (Spotpicker, Amersham), chopped into small pieces, washed with 100 mM $NH_4HCO_3$ pH 8.15 for 10 min, dehydrated with acetonitrile for 10 min, dried in speed vacuum, and re-swelled on ice with 10 ng/μl of trypsin in 50 mM $NH_4HCO_3$ for 45 min. After incubation the excess trypsin is removed and replaced with 50 mM $NH_4HCO_3$ and the samples are allowed to digest overnight at 37° C. Peptides are extracted with 50 μl of 50 mM $NH_4HCO_3$ and then three times with 5% formic acid, 50% acetonitrile. Each extraction is allowed to proceed 20 min. Samples are then lyophilized for MALDI-TOF and LC-MS/MS to identify proteins.

EXAMPLE 3

Identification of Erythrocyte O-GlcNAcylated Proteins

Nanobore reverse phase HPLC is routinely used directly into an ion-trap mass spectrometer (LCQ), MS/MS, TurboSequest or BioWorks software, with manual confirmation of spectral interpretations, to identify low abundance proteins and to map O-GlcNAc or phosphoryation sites.

Using samples from the JHMI Diabetes Center, it was determined how to remove hemoglobin from human erythrocytes, without the loss of the O-GlcNAcylated proteins of interest. Interestingly, it was observed that hemoglobin itself is O-GlcNAcylated. Initial studies used gel filtration on Superdex 200 (10/30) to both remove hemoglobin and separate erythrocyte proteins. OGlcNAcylated proteins were identified by western blotting with a pan-specific anti-O-GlcNAc antibody (CTD 110.6).

Since O-GlcNAc is very difficult to detect by standard mass spectrometric methods, a tagging method that is based upon earlier work on the use of galactosyltransferase to probe for OGlcNAc was employed. The modified method uses a mutant enzyme that can transfer a ketone-modified sugar. This ketone-sugar moiety then can be tagged using biotin hydrazide to allow for affinity chromatorgrapy to 'fish-out' O-GlcNAcylated proteins.

A related method, in which unmodified galactose is transferred enzymatically by galactosyltransferase to O-GlcNAc and then oxidized by galactose oxidase was also developed to allow for tagging with biotin-hydrazide. This approach was also used to identify erythrocyte O-GlcNAcylated proteins. Using these combined tagging approaches, together with MS/MS proteomics, at least thirty proteins in human erythrocytes were identified that are dynamically O-GlcNAcylated (Table 1). This identification was confirmed on several of the proteins by immunoprecipitation followed by western blotting using a pan-specific anti-OGlcNAc antibody.

Figure 2:
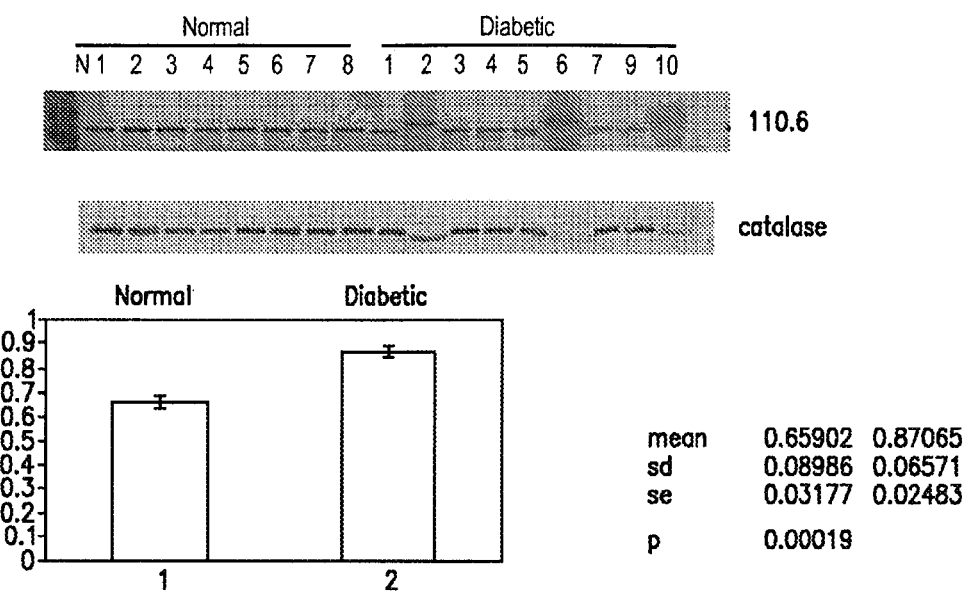
FIG. 2 is a pictorial and graphical diagram showing that O-GlcNAcylation is increased on catalase in human erythrocytes from diabetics.

After the identification of O-GlcNAcylated proteins, quantitative immunoprecipitation of selected proteins was then used in conjunction with western-blotting with anti-O-GlcNAc antibody to determine if the overall O-GlcNAcylation of the protein was quantitatively different between diabetic and normal erythrocytes. FIGS. 1 and 2 illustrate these studies.

TABLE 1

O-GlcNAcylated Proteins in Human Erythrocytes

| Protein description | Mass (Da) | NCBI entry | Coverage % | Peptides # |
|---|---|---|---|---|
| UDP-Gal-Ketone method | | | | |
| Catalase | 59947 | Gi4557014 | 12% | 12 |
| Aminolevulinic acid dehydrase Isoform b | 37718 | Gi34577066 | 5% | 2 |
| Protease, serine, 2 preproprotein | 26927 | Gi61097912 | 9% | 11 |
| Beta globin | 16102 | Gi4504349 | 68% | 19 |
| Peroxiredoxin 2 isoform a | 22049 | Gi32189392 | 49% | 17 |
| Phosphatase and actin regulator 2 | 69762 | Gi7662248 | 2% | 8 |
| Hypothetical protein XP_291007 | 166254 | GI51460838 | 1% | 14 |
| Homeo box HB9 | 40999 | Gi38348183 | 10% | 2 |
| Coagulation factor V precursor | 252702 | Gi4503643 | 1% | 8 |
| Potassium channel tetramerisation Domain containing 18 | 47223 | Gi45387953 | 3% | 3 |
| Organic cation transporter like 3 | 61435 | Gi4758852 | 10% | 2 |
| Peroxiredoxin 1 | 22324 | Gi4505591 | 10% | 8 |
| Alpha 2 globin | 15305 | Gi4504345 | 35% | 12 |
| Ubiquitin carrier protein | 24285 | Gi7657046 | 3% | 6 |
| Vacuolar protein sorting 13B isoform 2 | 161849 | Gi35493719 | 2% | 2 |
| Delta globin | 16159 | Gi4504351 | 44% | 17 |
| Cytochrome P450, family 3 | 58118 | Gi12383060 | 2% | 5 |
| Hypothetical protein XP_378876 | 33510 | Gi51458600 | 9% | 2 |
| Apurinic/apyrimidinic endonuclease 2 | 58390 | Gi18375507 | 4% | 14 |

TABLE 1-continued

O-GlcNAcylated Proteins in Human Erythrocytes

| Protein description | Mass (Da) | NCBI entry | Coverage % | Peptides # |
|---|---|---|---|---|
| Additional 110.6 reactive protein bands | | | | |
| Spectrin alpha, erythrocytic | 282024 | Gi4507189 | 3% | 11 |
| Spectrin beta isoform a | 268630 | Gi67782321 | 3% | 17 |
| Spectrin beta isoform b | 247171 | Gi67782319 | 3% | 17 |
| Glycogen phosphorylase | 97487 | Gi5032009 | 1% | 2 |
| c-AMP specific phosphodiesterase | 83918 | Gi32171241 | 2% | 1 |
| HSP90 alpha | 98622 | Gi63029937 | 7% | 12 |
| Protein Band3, erythrocytic | 102013 | Gi4507021 | 4% | 9 |
| N-acylaminocyl-peptide hydrolase | 82142 | Gi23510451 | 12% | 38 |
| Aldehyde dehydrogenase 1A1 | 55454 | Gi21361176 | 4% | 11 |
| Attractin isoform 1 | 163450 | Gi21450861 | 3% | 4 |
| UPD-Gal oxidase method | | | | |
| GPDH | 36201 | Gi7669492 | 23% | 15 |

EXAMPLE 4

BEMAD Quantification of O-GlcNAc Changes at Single Sites

Site-mapping of O-GlcNAc or even its detection by electrospray or MALDI MS is difficult since the sugar easily falls off or glycopeptide ions are suppressed at voltages or conditions normally used for peptides. In fact, mapping or detecting O-GlcNAc directly by mass spectrometry is many fold more difficult than detecting phosphorylation. The method for semi-quantitative site-mapping of O-GlcNAc, BEMAD, involves β-elimination, Michael addition with density tagged DTT and thiol-affinity enrichment of DTT-tagged proteins or peptides. A major advantage of DTT is that density labeled DTT is inexpensive, and most importantly the tag is stable to mass spectrometry and does not alter peptide fragmentation.

To increase coverage, proteins are fractionated into ~20 fractions, by preparative SDS-PAGE. Control and experimental samples will be ran on adjacent lanes, and identical gel sections will be taken from control and experimental samples. In general, the presence of O-GlcNAc does not affect the migration of proteins on 1D or even 2D-gels. Each gel fraction is "spiked" with an internal standard phospho-peptide and a O-GlcNAc-peptide, and is digested with trypsin. Tryptic peptides are performic acid oxidized, treated with alkaline phosphatase to remove any phosphorylation sites, and subjected to very mild alkali-induced β-elimination of the O-GlcNAc. The resulting dehydro amino acid is then subjected to Michael addition by dithiothreitol. Control samples will be tagged with light DTT, and experimental samples will be tagged with heavy DTT (d6) DTT-tryptic peptides are affinity enriched by thiol chromatography and sites are mapped by MS/MS and quantified by the ratios of light to heavy DTT (M/Z=136 of the DTT (light) and M/Z=142 (deuterated) adduct). Preliminary studies indicate that quantitation is typically accurate to about +/−10%.

SDS-PAGE, Coomassie Staining, and Western Blotting—SDS-PAGE will be performed under reducing conditions on precast 10% Criterion gels (Bio-Rad) with Coomassie G-250 staining. In early studies, we will perform Western blotting with antibody to O-GlcNAc to evaluate the fractionation of O-GlcNAc modified proteins. Western blotting of one-dimensional gels with 110.6 antibody has been described previously.

In-gel Digestion—Coomassie G-250-stained bands will be excised, dehydrated with acetonitrile, and re-swelled in 40 mM ammonium bicarbonate with 10 ng/ul trypsin (Promega) on ice for 45 min. After excess trypsin is replaced with 40 mM ammonium bicarbonate, digestion is allowed to proceed overnight at 37° C. The peptides are extracted three times for 20 min in 5% formic acid, 50% acetonitrile and dried down in a Speed Vac.

Performic Acid Oxidation, Phosphatase and N-Acetylglucosaminidase Treatment—Dried tryptic samples will be spiked with 20 pmoles of O-GlcNAc-BPP (PSVPVS(O-GlcNAc)GSAPGR (SEQ ID NO:41)) peptide and with 20 pmoles of phosphoryl-AKT peptide (KHFPQFS(P)YSAS (SEQ ID NO:42)), and then subjected to performic acid (5% hydrogen peroxide and 44% formic acid) for 1 h on ice. Oxidized peptides will then be digested with alkaline phosphatase (1 U/10 µl alkaline phosphatase containing 1 mM $MgCl_2$, 0.1 mM $ZnCl_2$) for 3 h at 37. In some cases, as a control, equal aliquots of samples will be treated with both alkaline phosphatase and β-N-acetylglucosaminidase (1 unit/ 20 µl, New England Biolabs) for 16 h at 37° C. after acidification with trifluoroacetic acid to pH 4.5 in order to validate the specificity of the thiol-affinity enrichment and to detect the presence of other unknown modifications attached to serine or threonine moieties.

BEMAD Modification—The original BEMAD methods were modified to improve the yield obtained from extraordinarily difficult peptides in which the O-GlcNAc moiety is surrounded by proline residues, as it is at Thr58 on the c-Myc oncogene. Yields of DTT modification of peptides approach 100% on many peptides and are ~50% on the most difficult peptides. With these difficult peptides containing multiple proline residues adjacent to the glycosylation site, 50% yield was obtained, due to severe peptide degradation with harsher conditions. Performic acid oxidized peptides are redissolved in 25 mM $Ba(OH)_2$ and the pH is checked. The samples are incubated at 50° C. for 4-8 hours under argon. The $Ba(OH)_2$ is precipitated with $CO_2$, and the samples are buffered with 25 mM $Na_2CO_3$. Michael addition is then performed with 100 mM DTT under argon at 37° C. for 48 hours. Control samples are labeled with light DTT (d0) and the experimental samples with heavy DTT (d6). The control and experimental samples are then combined and enriched by thiol affinity chromatography (see below) before LC-MS/MS analysis.

Thiol Affinity Chromatography—DTT-modified peptides are purified over activated thiol-Sepharose (thiol column) from Amersham Biosciences. Resin is swelled in degassed PBS containing 1 mM EDTA (PBS/EDTA), and dried peptides suspended in the same buffer are bound with a 1 h incubation in 200 μl of 50% slurry. The column is washed with 15 ml of PBS/EDTA and eluted three times sequentially with 150 μl of PBS/EDTA containing 20 mM free DTT. Peptides eluted from thiol affinity columns are acidified (brought to 1% trifluoroacetic acid), desalted with reverse-phase C18 spin columns (eluted in 70% acetonitrile, 0.1% trifluoroacetic acid), and dried for subsequent analysis.

MALDI Analysis—Peptide samples are resuspended in matrix (10 mg/ml alpha-cyano-4-hydroxycinnamic acid in 0.3% trifluoroacetic acid, 60% acetonitrile) and analyzed in reflector or linear mode on an Applied Biosystems Voyager DE STR MALDI instrument.

LC-MS/MS Analysis—Peptides are resuspended in 1% acetic acid and loaded on a 10-cm×0.075-mm nanobore column packed with 5 micron diameter beads of C18 resin using positive $N_2$ pressure, desalted with 1% acetic acid, and then separated via a 75-min linear gradient of increasing acetonitrile at a flow rate of ~200 nl/min directly into the source (Finnigan LCQ). The LCQ will typically be run in automatic mode collecting a MS scan (2×500 ms) followed by two MS/MS scans (3×750 ms) of the two highest intensity peptides with a dynamic exclusion set at 2 with a mass gate of 2.0 daltons. However, conditions are manually monitored to achieve maximum detection and sequencing of O-GlcNAc (DTT-modified) peptides.

Turbosequest or BioWorkds software will be used to help interpret MS/MS data. However, all assignments are confirmed manually. For DTT-modified peptides, a mass increase of 136.2 is allowed on serines and threonines. Samples that are treated with performic acid are allowed for oxidation of cysteine (48.0 daltons), tryptophan (32.0 daltons), and methionine (32.0 daltons). Changes in the extent of O-GlcNAcylation will be determined by the ratios of light and heavy DTT on the peptides. Only changes on sites (or lack of) seen reproducibly in multiple independent experiments will be taken to the next stage of the project. In every sample, there will be several proteins in which the ratio of light and heavy DTT is constant. Thus, in addition to the internal standard peptides, these sites will provide for internal calibration. These studies will determine relative changes in O-GlcNAcylation not absolute changes.

EXAMPLE 5

O-GlcNAcylation at Individual Sites

In order to perform the analyses required to determine if site-specific changes in O-GlcNAcylation are indeed predictive of early diabetes, a quantitative glycomic method was developed to measure site occupancy. The method simultaneously detects, locates and measures relative occupancy at the specific site level O-GlcNAc modified proteins.

Figure 3:
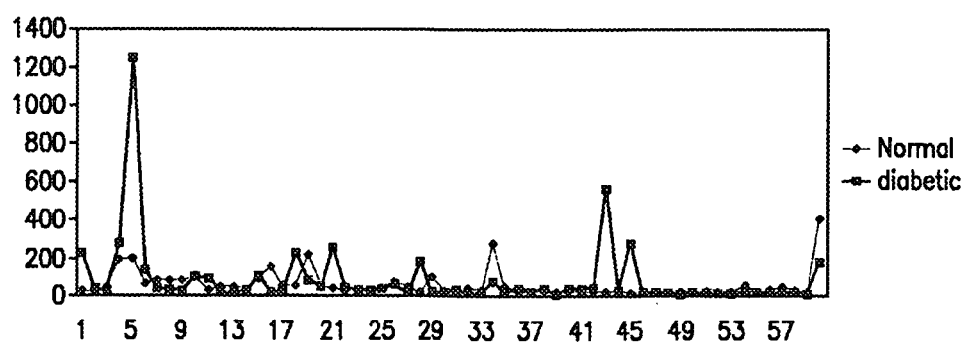
FIG. 3 is a graphical diagram showing site O-GlcNAcylation of a protein. The protein was O-GlcNAc enzymatically labeled via UDP-[3H]Gal and galactosyltransferase, subjected to trypsin and tryptic glycopeptides resolved by HPLC. (Note that O-GlcNAc is higher on some tryptic peptides).
Figure 4:
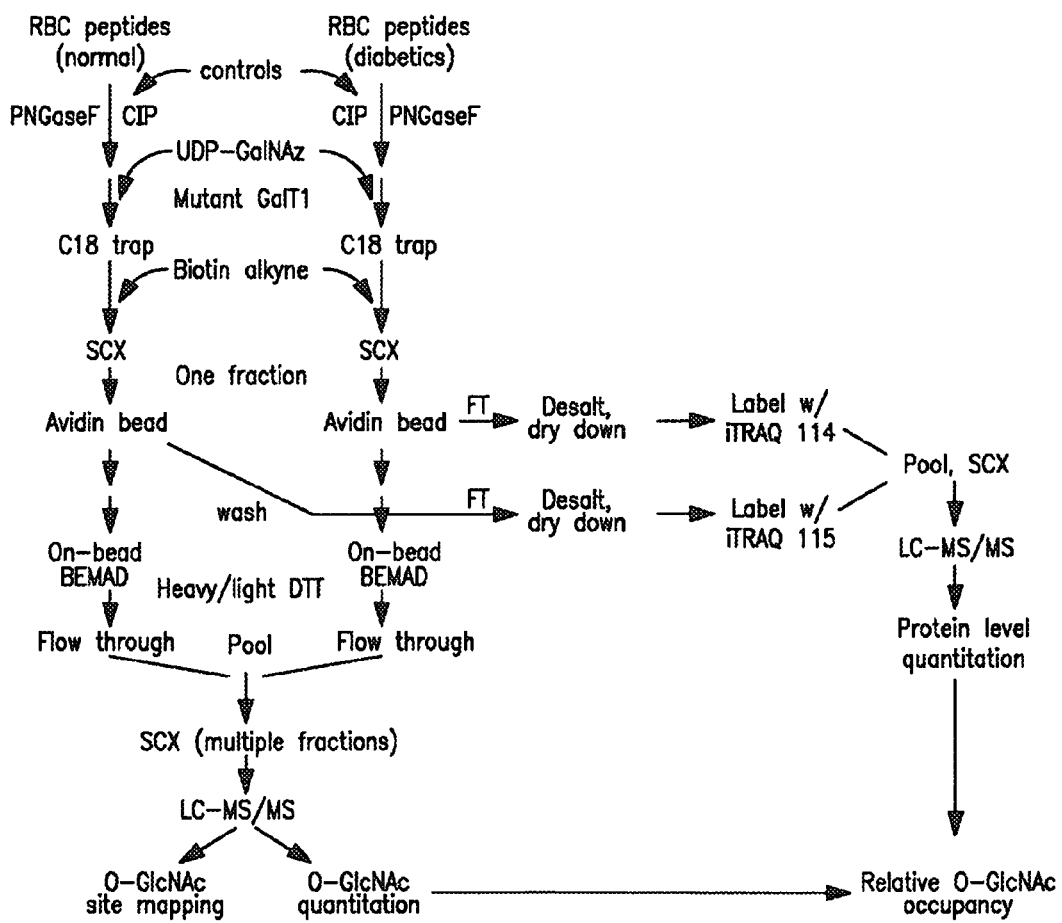
FIG. 4 is a graphical diagram showing the quantitative glycomics used to detect site-specific changes in GlcNAcylation in normal versus diabetic red blood cell proteins.

As shown in FIG. 3, O-GlcNAcylation at individual sites is a more sensitive measure of the diabetic state. FIG. 4 illustrates the quantitative glycomics to detect site-specific changes in GlcNAcylation in normal versus diabetic red blood cells (RBC). Tryptic peptides are prepared from Hb-depleted RBC. Control glyco- & peptides were added. N-glycans & phosphate are removed. GalNAz is enzymatically attached to GlcNAc-peptides, coupled to biotin. Avidin/Biotin selects GlcNAc peptides. On column BEMAD and MS/MS, in conjunction with density tagged DTT are used for quantitative site comparisons.

Figure 5:
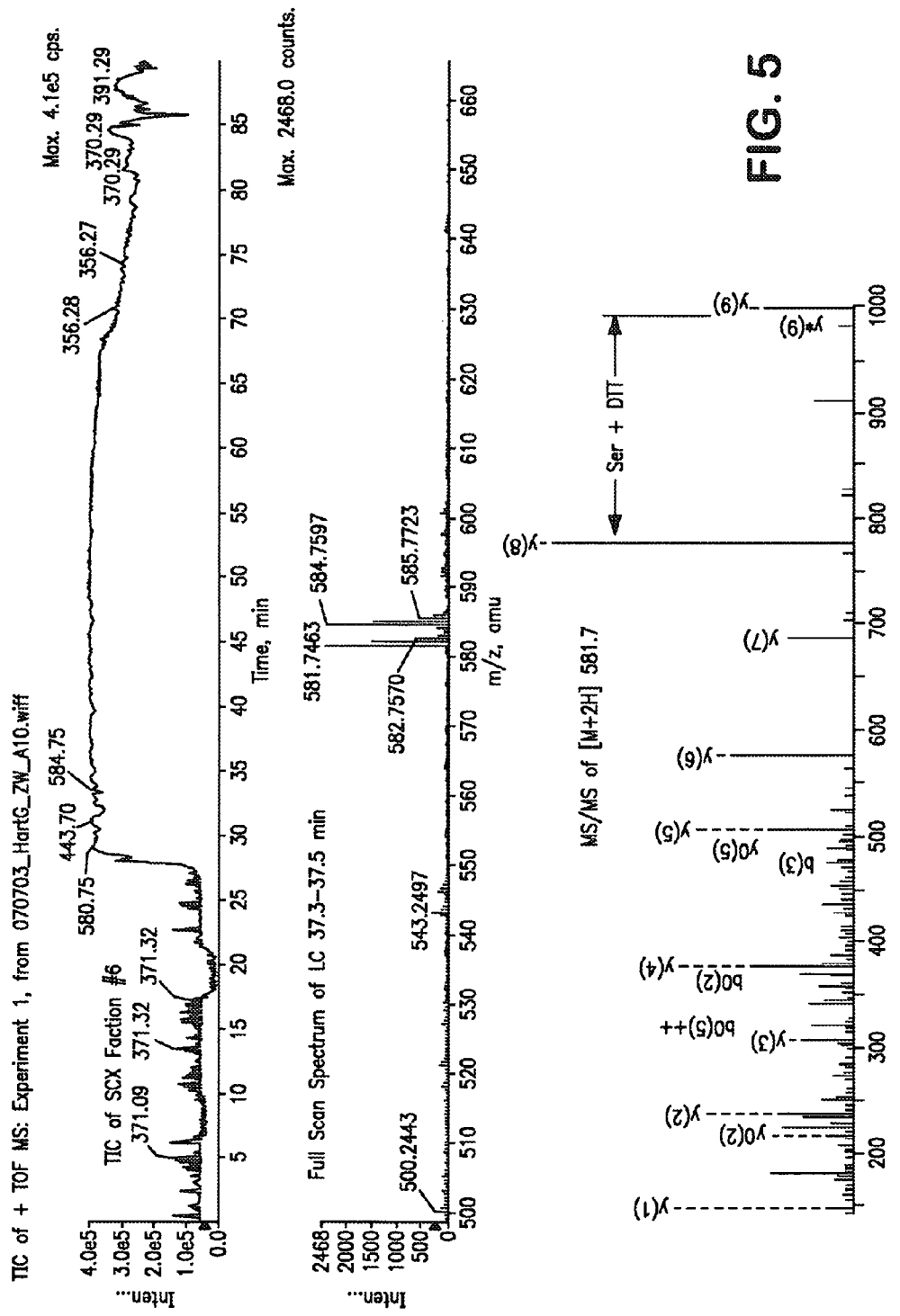
FIG. 5 is a graphical diagram showing an example of an O-GlcNAc site on K.YSLAEAASK.A (SEQ ID NO: 27) that doesn't change in diabetic versus normal RBC samples. Top=Total Ion Current; Middle=Full Scan of Region with Peptide; Bottom MS/MS Sequencing.
Figure 6:
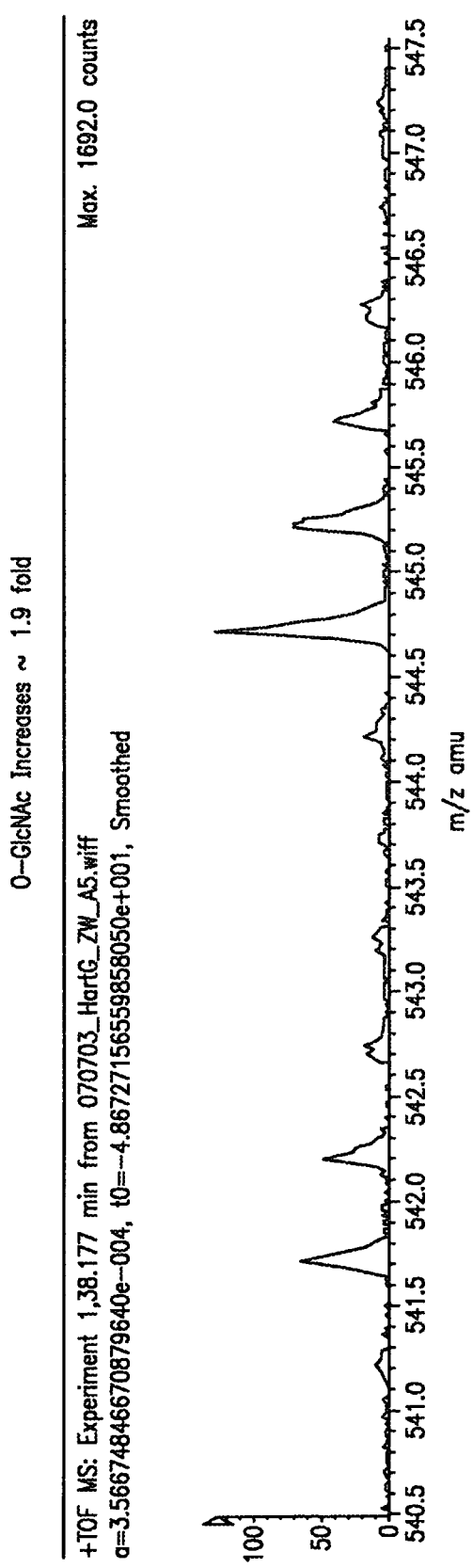
FIG. 6 is a graphical diagram showing a blow-up of Full Scan Spectrum of site 2 at K.NGPEQWSK.L (SEQ ID NO: 26) of the same protein as in FIG. 5, carbonic anhydrase from Normal and Diabetic RBC.
Figure 7:
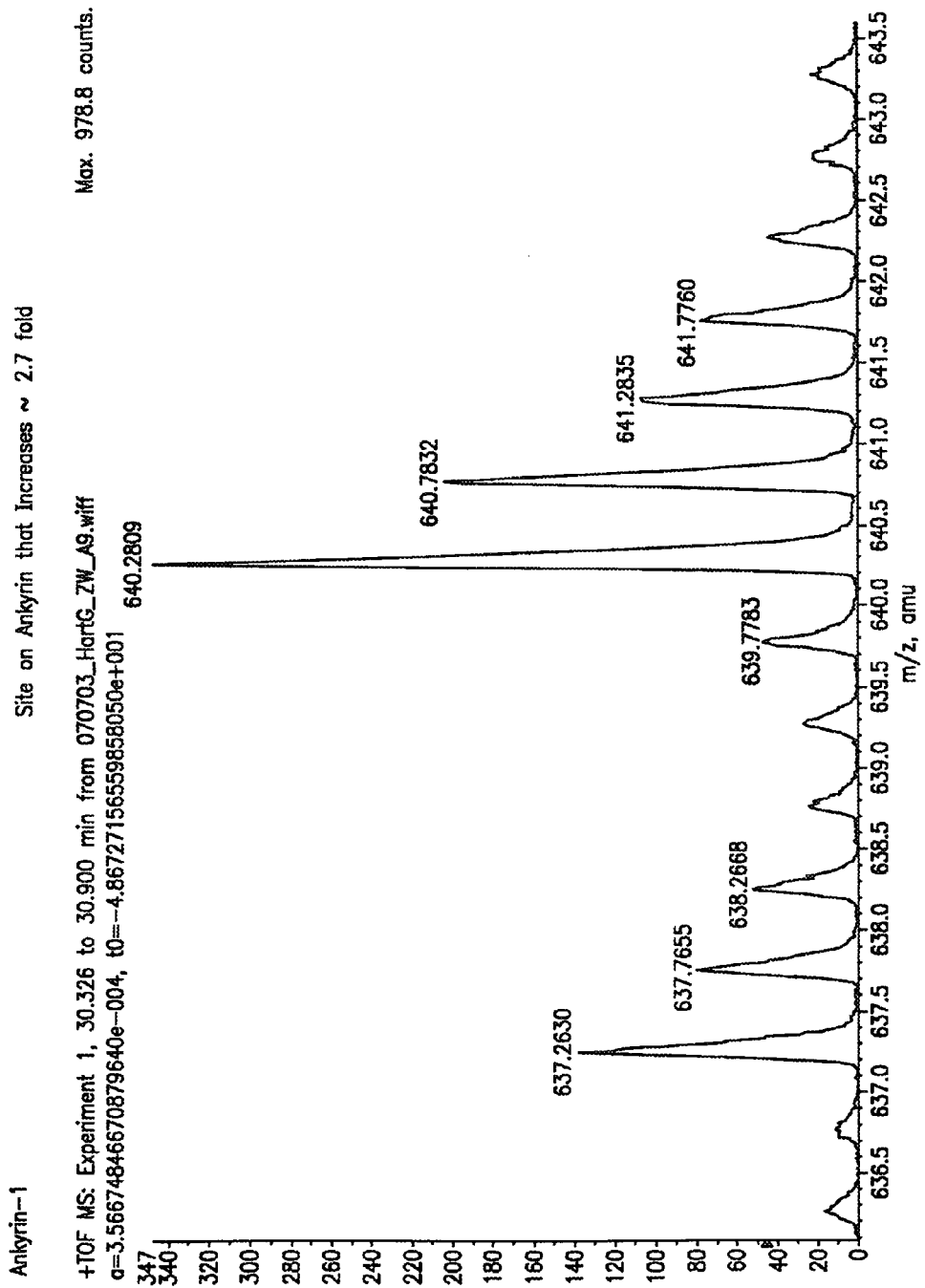
FIG. 7 is a graphical diagram showing Full Scan Spectrum of site on ankyrin that is 2.7-fold more GlcNAcylated at R.D SGEGDTTSLR.L (SEQ ID NO: 5) in Diabetic RBC. (Normals are light DTT tagged; Diabetics heavy DTT tagged).

FIG. 5 shows an example of an OGlcNAc site that doesn't change in diabetic versus normal RBC samples. Simultaneous detection of sites that don't change and those that do, especially on the same protein, validates this approach. FIG. 6 shows another site on the same protein, carbonic anhydrase, that is different between normal and diabetic samples. Finally FIG. 7 shows a full scan of a site on Ankyrin that changes ~2.7-fold in diabetic RBC.

EXAMPLE 6

Site-Specific Protein O-GlcNAcylation

Five to ten O-GlcNAc sites that have a range of responsiveness to hyperglycemia will be identified. Site-specific antibodies to the O-GlcNAcylated site and the unmodified site will then be prepared. The O-GlcNAc dependent antibody will be tagged with a distinct color tag from the antibody recognizing the unmodified site. A third tagged antibody to actin to will also be used to normalize (normalization may not be necessary if only the ratios are compared). These antibodies will then be used to develop a rapid assay that can be performed in the laboratory.

The non-glycosylated form of each site chosen will also be prepared. Based upon these methods both corresponding, unmodified, glycopeptides, and phosphopeptides for RNA polymerase II, cytomegalovirus basic phosphoprotein (BPP), c-myc, casein kinase II and others were successfully synthesized. A list of proteins/sites identified by these experiments is provided in Tables 2 and 3.

TABLE 2

Mapping/Quantitation Results of Proteins

| Accession No. | Protein Name | O-GlcNAc Peptides | SEQ ID No. | Peptide Score | Ratio D/N |
|---|---|---|---|---|---|
| P16157 | Ankyrin-1 | K.LSTPPPLAEEEGLASR.I | 1 | 98 | 0.8 |
|  | (Erythrocyte ankyrin) | K.VVTDETSFVLVSDK.H | 2 | 47 | 1.5 |
|  |  | R.EPGGSLSFLR.K | 3 | 43 | 0.84 |
|  |  | R.ISEILLDHGAPIQAK.T | 4 | 49 | 1.1 |
|  |  | R.DSGEGDTTSLR.L | 5 | 45 | 2.7 |
|  |  | R.EADAATSFLR.A | 6 | 48 | 1.1 |
| P62736 | Actin, aortic smooth muscle | K.DSYVGDEAQSK.R | 7 | 60 | 1.8 |
|  |  | K.EITALAPSTMK.I | 8 | 48 | 1.5 |
|  |  | K.QEYDESGPSIVHR.K | 9 | 43 | 1.0 |
| P02549 | Spectrin alpha chain | R.VSSQDYGR.D | 10 | 53 | 1.0 |
|  |  | R.VILENIASHEPR.I | 11 | 42 | 1.0 |
|  |  | R.LSESHPDATEDLQR.Q | 12 | 50 | 1.0 |

TABLE 2-continued

Mapping/Quantitation Results of Proteins

| Accession No. | Protein Name | O-GlcNAc Peptides | SEQ ID No. | Peptide Score | Ratio D/N |
|---|---|---|---|---|---|
| P04406 | Glyceraldehyde-3-phosphate dehydrogenase | R.GALQNIIPAS<u>T</u>GAAK.A | 13 | 52 | 1.0 |
| P37837 | Transaldolase | R.V<u>S</u>TEVDAR.L | 14 | 38 | 0.9 |
| P32119 | Peroxiredoxin-2 | K.A<u>T</u>AVVDGAFK.E | 15 | 37 | 0.74 |
|  |  | R.L<u>S</u>EDYGVLK.T | 16 | 51 | 0.74 |
| P16452 | Erythrocyte membrane protein band 4.2 | R.TQATFPI<u>S</u><u>S</u>LGDR.K | 17 | 37 | 0.83 |
|  |  | R.G<u>S</u>VPILR.Q | 18 | 26 | 1.0 |
| P62937 | Peptidyl-prolyl cis-trans isomerase A | R.V<u>S</u>FELFADK.V | 19 | 44 | 1.1 |
| P11166 | GLUT1 | R.TFDEIA<u>S</u>GFR.Q | 20 | 59 | 1.1 |
| P07738 | Bisphosphoglycerate mutase | K.TILISAHGN<u>S</u><u>S</u>R.A | 21 | 24 | 1.0 |

Peptide score of 36 indicates identity (p < 0.05)
Two underlines in the same peptide mean either one of the two amino acids is O-AlcNac-modified, but not both.

TABLE 3

Mapping/Quantitation Results of Proteins

| Accession No. | Protein Name | O-GlcNAc Peptides | SEQ ID No. | Peptide Score | Ratio D/N |
|---|---|---|---|---|---|
| P11277 | Spectrin beta chain, erythrocyte | R.DV<u>S</u><u>S</u>VELLMK.Y | 22 | 56 | 1.0 |
|  |  | K.DL<u>T</u>SVLILQR.K | 23 | 43 | 1.1 |
|  |  | K.LLTSQDVSYDEAR.N | 24 | 69 | 1.2 |
|  |  | R.AQGLL<u>S</u>AGHPEGEQIIR.L | 25 | 54 | 1.0 |
| P00915 | Carbonic anhydrase 1 (EC 4.2.1.1) | K.NGPEQW<u>S</u>K.L | 26 | 51 | 1.9 |
|  |  | K.Y<u>S</u>SLAEAASK.A | 27 | 58 | 1.0 |
|  |  | K.GGPFSD<u>S</u>YR.L | 28 | 48 | 1.4 |
|  |  | K.ESI<u>S</u>VSSEQLAQFR.S | 29 | 86 | 1.3 |
|  |  | K.HD<u>T</u>SLKPISVSYNPATAK.E | 30 | 58 | 1.4 |
| P68871 | Hemoglobin subunit beta | R.FFESFGDL<u>S</u>TPDAVMGNPK.V | 31 | 53 | 2.0 |
|  |  | K.VLGAF<u>S</u>DGLAHLDNLK.G | 32 | 75 | 1.7 |
|  |  | K.G<u>T</u>FATLSELHCDK.L | 33 | 52 | 1.0 |
| P02730 | Band 3 anion transport protein (Anion exchange protein 1) | K.L<u>S</u>VPDGFK.V | 34 | 41 | 1.0 |
|  |  | K.NS<u>S</u>YFPGK.L | 35 | 53 | 1.1 |
|  |  | R.AAATLM<u>S</u>ER.V | 36 | 63 | 0.9 |
|  |  | K.A<u>S</u><u>T</u>PGAAAQIQEVK.E | 37 | 86 | 0.75 |
|  |  | K.IPPD<u>S</u>EATLVLVGR.A | 38 | 69 | 1.1 |
|  |  | R.YQ<u>S</u><u>S</u>PAKPDSSFYK.G | 39 | 42 | 1.0 |
| P30041 | Peroxiredoxin-6 (EC 1.11.1.15) | K.L<u>S</u>ILYPATTGR.N | 40 | 45 | 1.0 |

Peptide score of 36 indicates identity (p < 0.05)
Two underlines in the same peptide mean either one of the two amino acids is O-AlcNac-modified, but not both.

EXAMPLE 7

Selection of O-GlcNAc Sites to use for Antibody Production

The glycomic site mapping/quantification method will be performed on three sets of samples: 1) Normal and Overtly Diabetic Patients from JHMI that have been collected into tubes containing the potent OGase inhibitors NAG-thiazoline or PUGNAc; 2) NIH provided samples; 3) Samples similar to the NIH provided samples, but collected (or immediately transferred to) into tubes containing NAG-thiazoline or PUG-NAc. Collection in the immediate presence of these OGase inhibitors will prevent loss of O-GlcNAc during sample work-up.

EXAMPLE 8

Synthesis of O-GlcNAcylated Peptides for Antibody Production

This example prepares site-specific monoclonal antibodies to O-GlcNAc sites that cover the range of changes seen in normal, pre-diabetic and diabetic patients, ranging from no change in O-GlcNAc to the site that is most responsive to dysregulation in glucose homeostasis. Based upon the data obtained herein, chemically synthesized glycopeptides will be prepared to match the sites (from at-least ten sites). Selection of the site will be based upon the abundance and responsiveness of the modified site to hyper- or hypoglycemia. Sites will be selected to represent the total ranges of change from zero to the highest extent. Monoclonal antibodies specific for each site will be generated, screened, and validated for specificity and sensitivity. Based upon this method, a site-specific, O-GlcNAc-dependent monoclonal antibody to a key regulatory site (Thr58) on the c-Myc oncogene protein was prepared.

Figure 8:
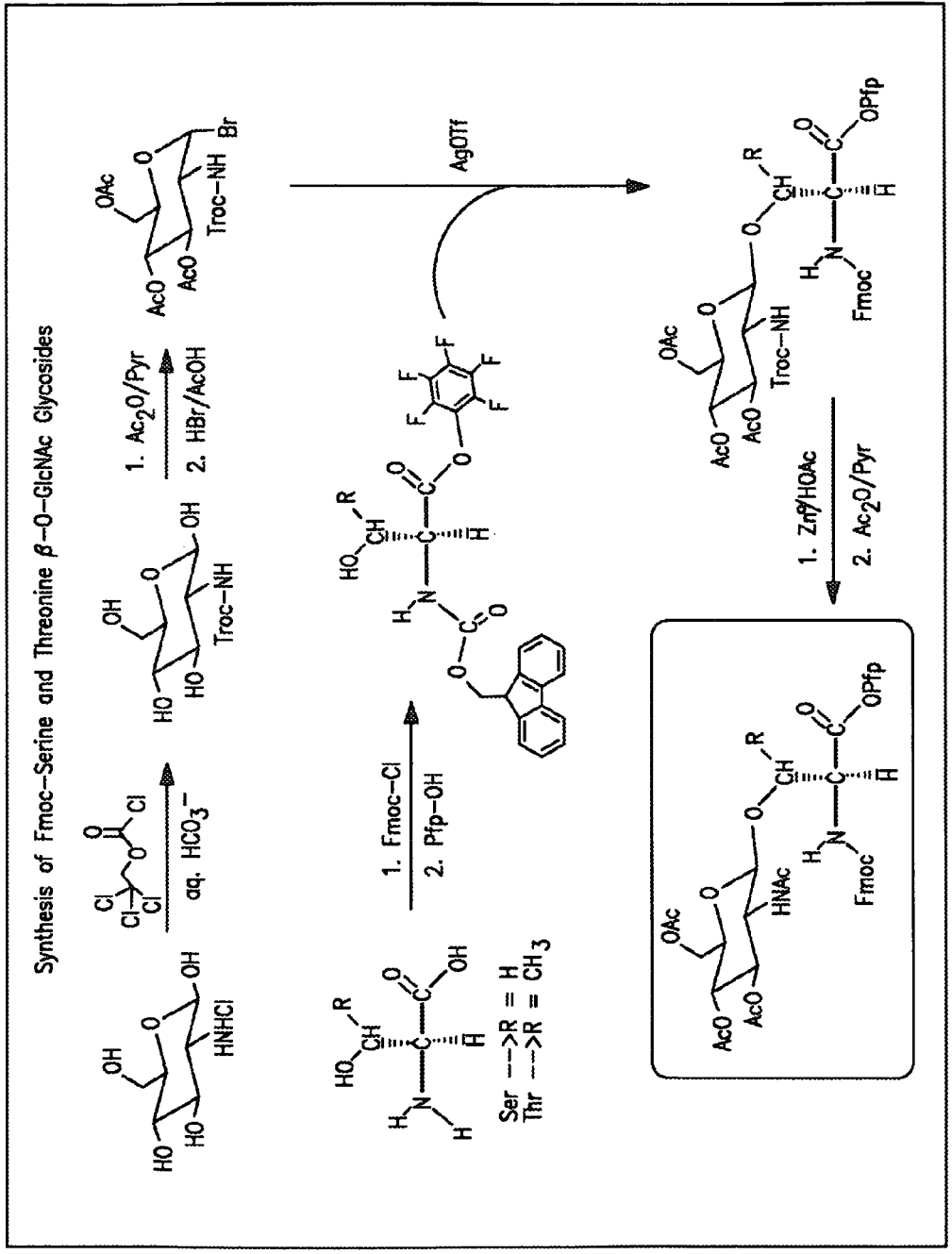
FIG. 8 is a schematic diagram showing the synthesis of Fmoc protected OGlcNAc-Ser(Thr) amino acids.

The procedure for synthesizing the protected glycol-amino acids for the solid-state synthesis of GlcNAcylated peptides is shown in FIG. 8. Once the protected fmoc-Ser(Thr)-O-GlcNAc is synthesized, the modified peptides are synthesized by standard solid-state chemistry with modified deprotecting reactions. Both site-specific and pan-specific anti-O-GlcNAc monoclonal antibodies will be prepared. O-GlcNAc is surprisingly immunogenic with the majority of monoclonal antibodies produced against nucleoporins having the saccharide as a major epitope. Recently, it has been shown that ~0.1% of all peptides presented with MHC antigens have O-GlcNAc attached, resulting in GlcNAc-peptide specific T cells.

Figure 9:
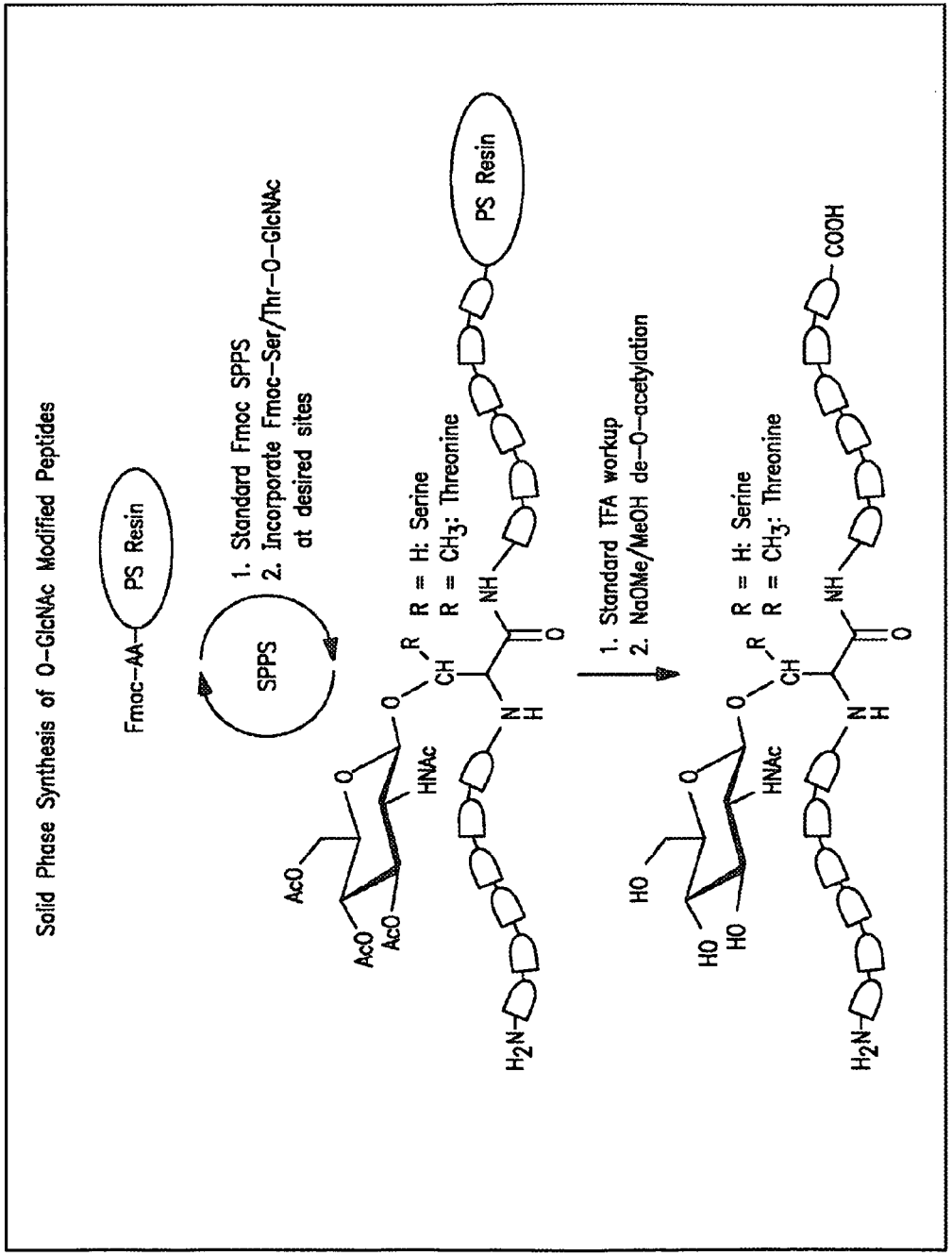
FIG. 9 is a schematic diagram showing the synthesis of O-GlcNAc modified peptides to make the site specific antibodies.
Figure 15:
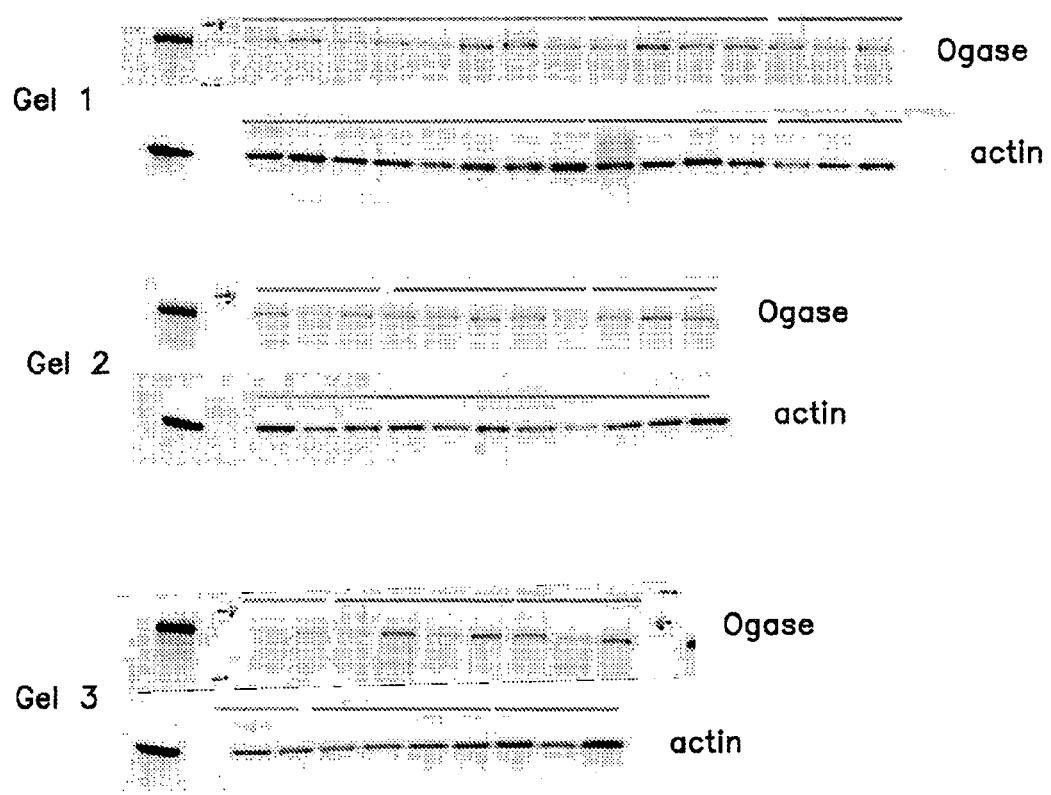
FIG. 15 is a pictorial diagram showing Western blotting of O-GlcNAcase from Normal, Pre-diabetic and Diabetic Samples (NIH), normalized to actin. The results shown are from Ogase in red blood cells, 90 µg protein, Hb-depleted, 10% gel.

As shown in FIG. 9, ~15 mer peptides with the O-GlcNAc residue near the center will be used as antigens to elicit site specific antibodies. Screening for antibodies that only recognize the modified or the naked site but not both, will be performed, as described herein.

Each peptide will be made to contain a cysteine residue at its N-terminus. Peptides will be coupled to KLH for use as immunogen, by using the bifunctional reagent N-hydroxysuccinimide ester of N-(carboxy cyclohexyl-methyl)-maleimide (smcc; Sigma) and a standard two-step protocol (Sun, et al., (2003) Preparation and Application of Polyclonal and Monoclonal Sequence-Specific Anti-Phosphoamino Acid Antibodies *Current Protocols in Protein Science* 2, 13.16.11-13.16.27). First, KLH is coupled to smcc by reacting the succinimide moiety of ssmc with amine groups on KLH. Second, smcc-modified KLH is reacted with the glycopeptide containing the N-terminal cysteine residue, linking the maleimide of smcc-KLH to the sulfhydryl of the glycopeptide and excess unlinked peptide is removed by gel filtration. If any peptides have multiple cysteine residues or have a cysteine near the site of O-GlcNAcylation, the peptide will be coupled using published glutaraldehyde or carbodiimide methods.

Primarily to use in screening, but also to use as an immunogen, if cysteines are problematic, peptides will also be coupled to BSA. A 30 molar excess of O-GlcNAc peptide will be dissolved in water, pH ad-justed to neutral and coupled to BSA using glutaraldehyde (Doolittle, (1986) *A Primer on How to Analyze Derived Amino Acid Sequences*, University Science Books, Mill Valley, Calif.).

EXAMPLE 9

Preparation of O-GlcNAcylation Dependent Site-Specific Antibodies

This example demonstrates preparation of a battery of highly specific and high-affinity monoclonal antibodies to the various glycopeptides synthesized. Concomitantly, antibodies to the unmodified site will also be prepared, both for possible use in diagnostics and as controls for O-GlcNAc dependence and for validating the specificity of the antibodies. It is clear that blockage of antibody reaction to the peptide by O-GlcNAcylation may be as useful as direct recognition of the saccharide as a diagnostic tool. The methods will be based upon the successful schemes developed for phosphopeptide antibodies.

Sites to which sequence-specific O-GlcNAc-amino acid antibodies are to be made and chemically synthesize the glyco-peptides will be selected. The glyco- and unmodified pep-tides (12 to 15 amino acids with O-GlcNAc site at the center and a cysteine residue at the N-terminus) will then be cross-linked to carrier proteins. Keyhole limpet hemocyanin (KLH) conjugates will be used as immunogen and bovine serum albumin (BSA) conjugates will be used for ELISA screening.

Injection of mice for monoclonal antibody production will follow standard methods. Cross-linked glycopeptides and peptides will be used as immunogens by repeated subcutaneous, followed by I.V., and intraperitoneal injections into A/J or BALBc mice until high titers are observed by ELISA assays. After approximately five immunizations in BALB/c mice (generally 50-60 days), cells from the popliteal and inguinal lymph nodes of mice with the highest titers will be collected and fused with the P3X63Ag8.653 myeloma line according to the standard procedures. Epitopes screened by ELISA will consist of the cognate non-glycosylated peptide, the O-GlcNAc cognate peptide, and an unrelated O-GlcNAc peptide. After the HAT selection, supernatants will be screened for reactivity with respective antigen. Confirmation of specificity will be obtained by dot-blot analysis, and Western-Blotting to both 1D and 2D gels. Clonal hybridoma supernatants will then be screened as provided above. Positive and specific hybridomas will then be expanded and frozen.

ELISA screening—Assays will employ standard 96-well format. Bound monoclonal antibodies will be detected using biotinylated horse anti-mouse secondary antibody followed by horseradish peroxidase conjugated avidin and 4-aminoantipyrine/$H_2O_2$. Binding to the following will be determined: 1) cognate non-glycopeptide-BSA conjugate; 2) unrelated O-GlcNAc peptide; 3) cognate O-GlcNAc peptide.

Monoclonal antibodies will be characterized for isotype, specificity and sensitivity. Isotype will be determined by standard methods. Prior to working with the antibodies, they will be affinity purified on protein-A or protein-G Sepharose, and antigen affinity purified on a cognate peptide or glyco-peptide affinity column. Specificity and sensitivity of each antibody will first be confirmed by ELISA assays and then by dot blotting, and by western blotting 1D and 2D gels. The minimum stoichiometry (O-GlcNAc site occupancy/nano-mole/site and polypeptide mass) detectable for each site specific antibody will then be determined using pure glycopeptides, and re-combinant glycoproteins.

EXAMPLE 10

O-GlcNAcase is Elevated in Erythrocytes from Diabetic Patients

Figure 10:
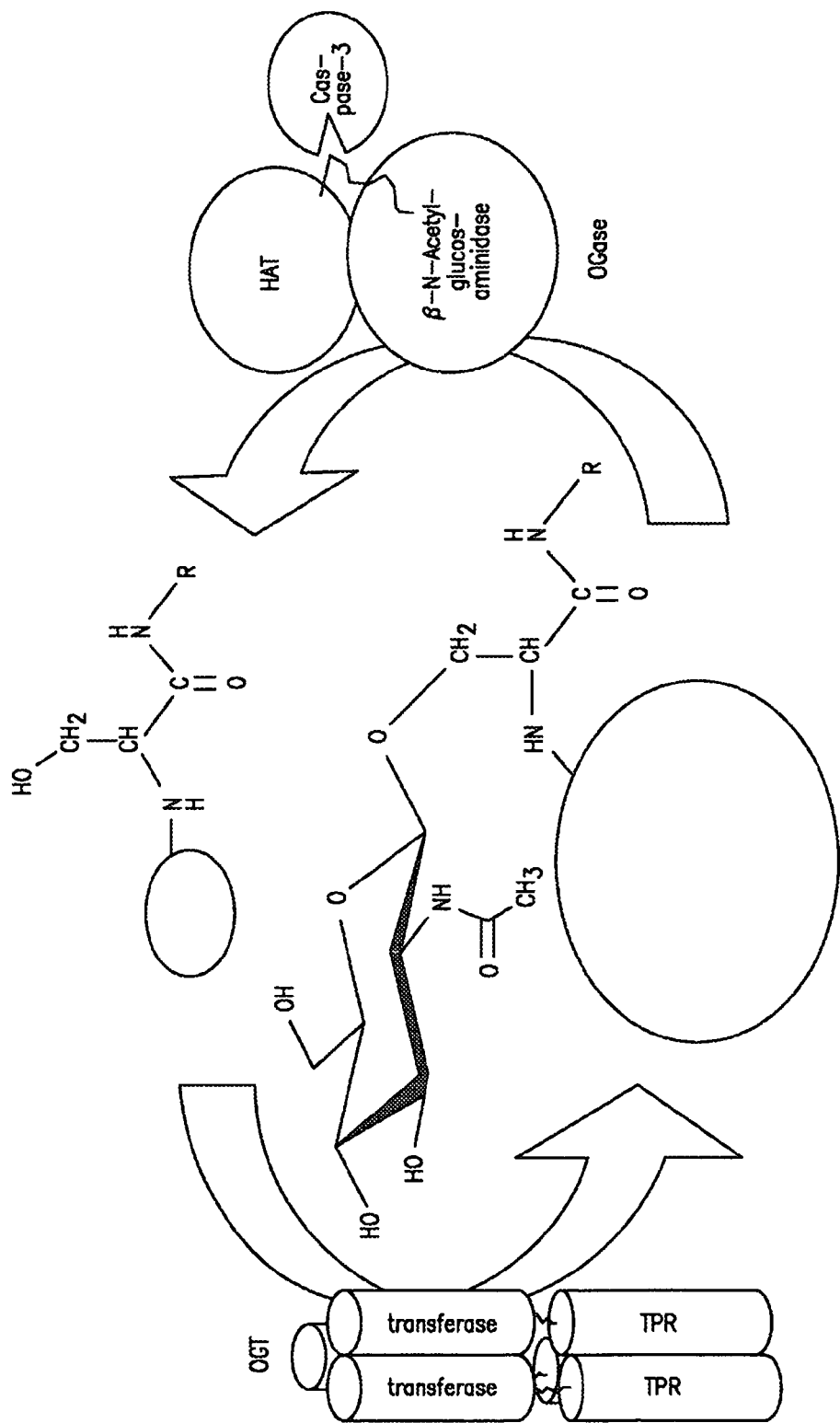
FIG. 10 is a pictorial diagram showing that cycling of O-GlcNAc is controlled by OGT and OGase.
Figure 11:
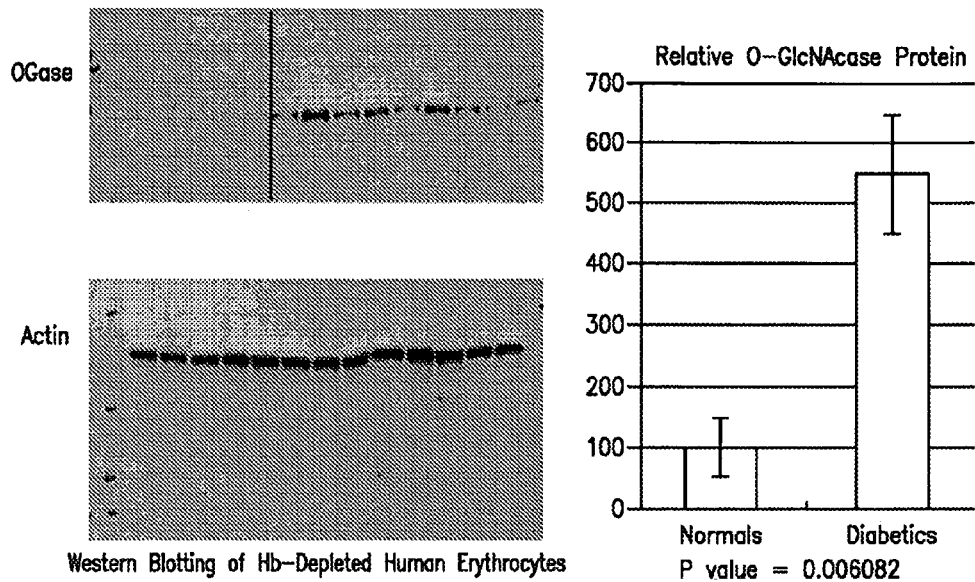
FIG. 11 is a pictorial and graphical diagram showing that O-GlcNAcase is upregulated in red blood cells from Diabetic subjects.

During the preliminary studies provided above, it was observed that the enzyme that removes O-GlcNAc, OGlcNAcase is elevated in erythrocytes from diabetic samples (see FIG. 10). Several polyclonal antibodies have been prepared from both rabbits and chickens to both full-length O-GlcNAcase and its N-terminal and C-terminal caspase 3 fragments (FIG. 11).

Figure 12:
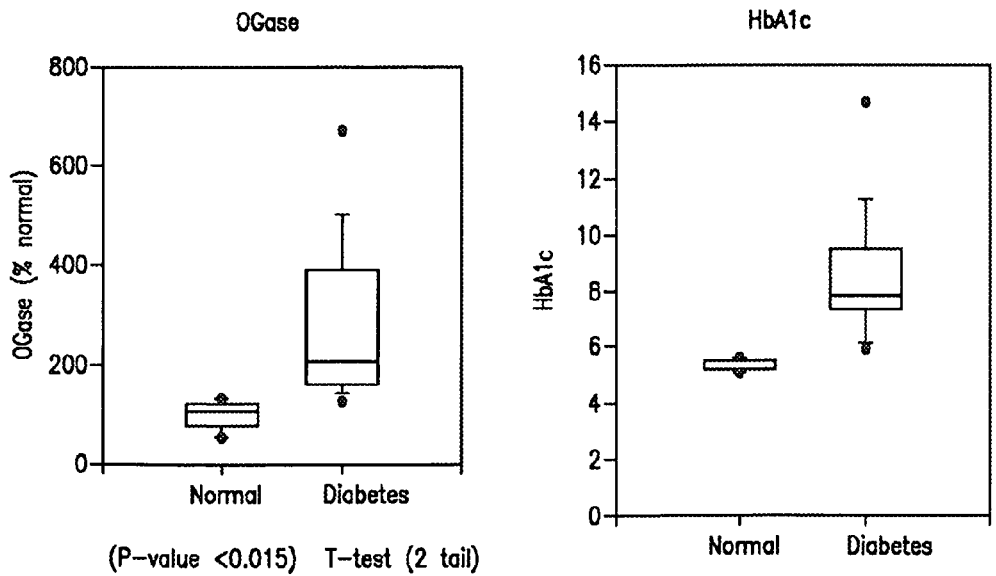
FIG. 12 is a graphical diagram showing that O-GlcNAcase protein levels increase in diabetic erythrocytes and reflect the characterization of diabetic state comparable to HbAlc.

These studies also indicated that O-GlcNAcase reflects the diabetic state in a manner that appears at least as good as the HbA1c test as described above (see FIG. 12).

EXAMPLE 11

Characterization of Hyperglycemia Based on O-GlcNAcase

This example demonstrates use of the antibodies obtained in Example 9 to develop simple clinically useful diagnostic tests for the analysis of patients, normal, pre-diabetic and diabetic. Using streptozotocin (STZ) rat blood samples and samples from patients, a quantitative ELISA, dot blot, dip stick, and simple 1D gel blot assays to correlate diabetic phenotype with O-GlcNAcylation state of blood proteins will be developed and validated.

Monoclonal-Polyclonal Sandwich Immunoassay—In a typical microtiter plate sandwich immunoassay, a monoclonal antibody is adsorbed onto a plastic microtiter plate. The test sample is added to the plate and the immobilized antibody binds the target antigen from the sample and retains it on the plate. A 'sandwich' is formed when a polyclonal antibody (with an attached detector) to the antigen is then added. Binding of the polyclonal is measured by radioisotopes in an RIA, enzymes which produce chromagens in EIA or ELISA.

Enzyme Immunoassays (EIA)—EIA methods combine the specificity of antibodies with the enormous amplification generated by enzyme catalysis, therefore can detect very small amounts of antigen. Most EIA assays are easily performed by individuals with little training. Direct EIA employ antibodies directly conjugated to an enzyme; whereas in indirect EIA the antigen-specific antibody is in-turn detected by an anti-immunoglobulin enzyme conjugate, of which a wide range are commercially available. Many indirect EIA formats use the strong interaction between avidin and biotin, allowing the same conjugate to be used to detect different antigens. Detection limits of these types of formats can be as low as 1 ng/ml.

Point of Care (POC) Assays—Dextran-Cyanin Dye Conjugates have been used in lateral flow assays type 'dipstick' assays. The Cy dyes give a line or spot signal that can be read by eye for 'yes/no' answers or read by a fluorometer for a quantitative answer. For qualitative analysis the Cy dyes give an intense blue color. Nitrocellulose strips with dextran-Cy Dye conjugated antibodies.

Current immunological based detection strategies include direct, and indirect methods. In direct methods, antigens are immobilized and detected with soluble labeled antibodies. In indirect methods, antibodies are immobilized and are probed with labeled proteins. In so-called sandwich methods, unlabeled antibody specific for antigens is immobilized to bind antigen, which is then probed by a second labeled antibody specific for the antigen. For example in the case of O-GlcNAc detection, an antibody could be bound to a specific O-GlcNAc protein to capture the protein and detect its O-GlcNAcylation state with a second site-specific antibody or even a pan O-GlcNAc specific antibody that is already on hand.

Ideal solid supports have common attributes: minimal autofluorescence, limited nonspecific binding, high surface area-to-volume ratio, inert to biological molecules and compatibility with available detection methods. Polyvinylidine difluoride (PVDF), nitrocellulose, aldehyde-treated glass, and various coated glass have been used extensively. Typically after immobilization of antibody or antigen, protein binding sites are blocked with dilute bovine serum albumin or casein.

ELISA—Commonly used enzymes for chromogenic detection in ELISA assays include horseradish peroxidase (HRP) and alkaline phosphatase (AP). Commonly used enzymes and substrates for chromogenic assays have been discussed in detail above.

Chemiluminescent Detection Methods—These methods are based upon chemiluminescent methods commonly used in Western blotting. Antigen-bound antibodies are detected with secondary antibodies conjugated to alkaline phosphatase or horseradish peroxidase. The enzymatic oxidation of substrates such as, luminol, produces emission of light which is detected by X-ray film or by a reader.

Fluorescence-based Detection—Cyanine dyes, e.g., Cy3 and Cy5, are commonly used for fluorescence detection strategies due to their inherent brightness, and reduced sensitivities to photobleaching and quenching.

Alexa Dyes—Recently, it has been reported that a new class of sulfonated coumarin and sulfonated rhodamine dyes, termed Alexa dyes, may be superior in many aspects to the cyanine dyes, particularly in terms of fluorescence emission and photostability. Alexa dyes are relatively insensitive to pH and some have higher molar extinction coeffcient than fluoresceins or rhodamines. Importantly, the water solubility of the succinimidyl esters of these dyes permit fairly high derivativzation without protein precipitation issues. Thus, in early studies, Alexa dyes will be used exactly as described for the cyanine dyes (above) to evaluate which is best for our long-term studies.

Figure 13:
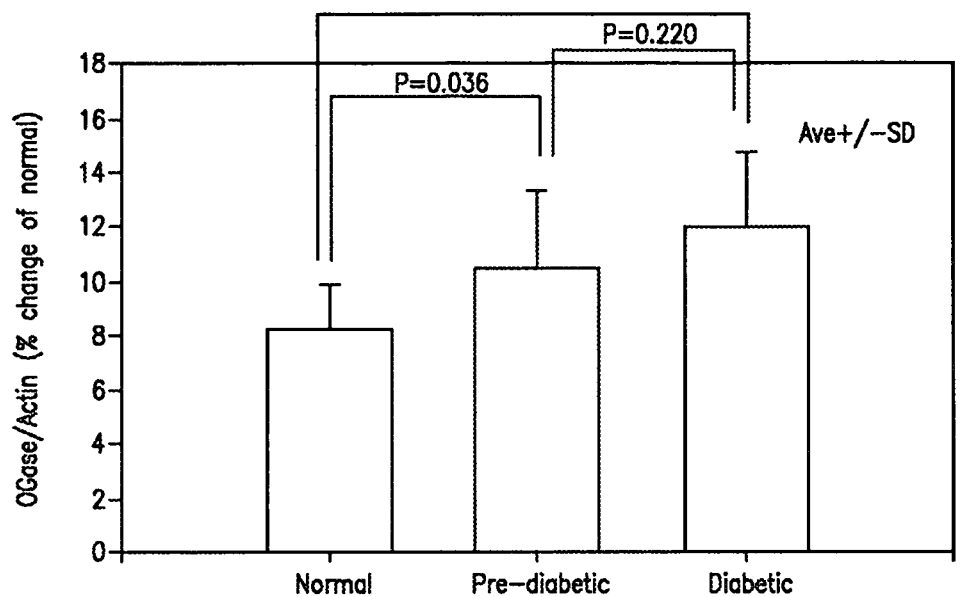
FIG. 13 is a graphical diagram showing a comparison of normal, pre-diabetic and diabetic samples using Western Blotting. The results shown reflect 12 normal, 12 pre-diabetic, and 9 diabetic samples (1 diabetic sample was duplicated for gel to gel comparison).
Figure 14:
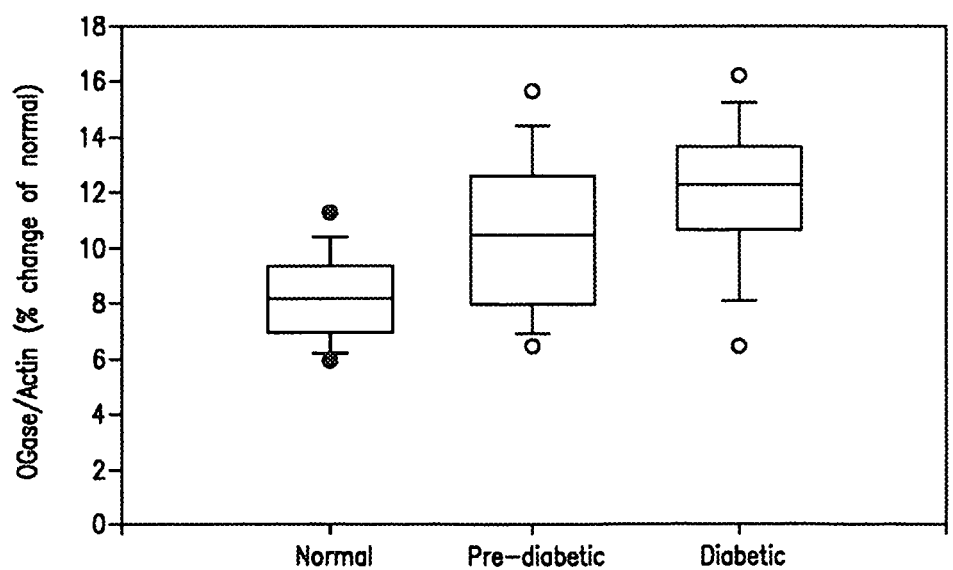
FIG. 14 is a graphical diagram showing a comparison of quantitation levels of Ogase among normal, pre-diabetic and diabetic samples using Western Blotting. The results shown reflect 12 normal, 12 pre-diabetic, and 9 diabetic samples (1 diabetic sample was duplicated for gel to gel comparison).

As shown in FIGS. 13 and 14, the levels of O-GlcNAcase do appear to correlate with the characterization of diabetic state, even in the 'pre-diabetic' (IFG) patient. Even using Western blotting, which has high backgrounds, very short dynamic range and poor sensitivity, the differences between OGlcNAcase levels between the samples is clear.

Figure 16:
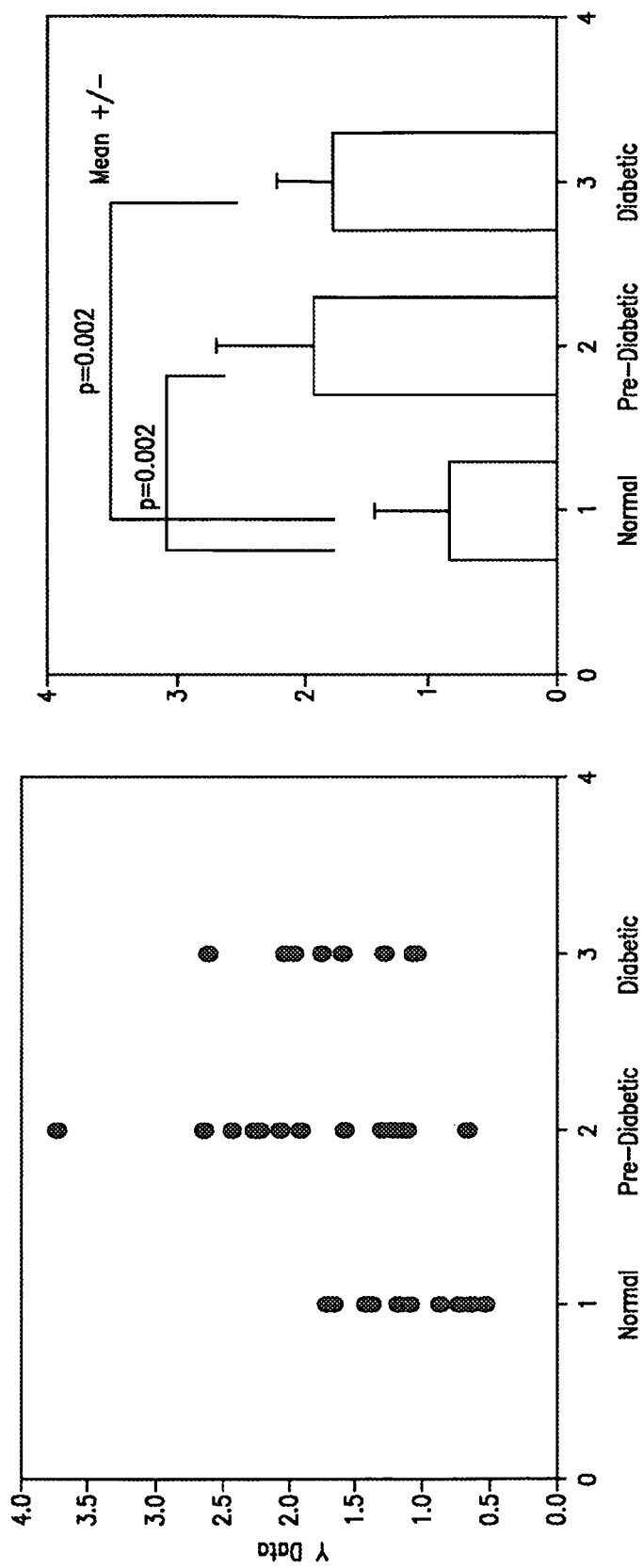
FIG. 16 is a graphical diagram showing quantitative comparisons of Western Blot Analyses of O-GlcNAcase Levels in samples.

FIG. 15 shows another example where Western Blotting using anti-O-GlcNAcase antibody can detect the prediabetic state (IFG), even when the HbA1c differences are small. Interestingly, as shown in FIG. 16, the major differences, seen in these studies, occurs between the 'prediabetics' and normal samples (p value=0.0028). In this assay, prediabetics, as defined by IFG and HbA1c, while different from normal, are similar to the full-blown diabetic patient samples in OGase levels.

During these studies, it was also found that pronounced elevations of O-GlcNAc occur on many proteins in white cells from human blood. In addition, it was observed that many proteins in human serum were O-GlcNAcylated. Since these serum proteins undoubtedly arise from damaged cells, their identification might be useful for monitoring specific tissue damage in disease. For example, O-GlcNAcylated troponin I, might be a sensitive monitor of damage to cardiac muscle.

EXAMPLE 12

Immobilized Antigen, Labeled Antibodies with Three color Relative Quantitation

Existing methods developed for protein microarrays will be adapted to begin to develop a rapid quantitiative assay for site-specific O-GlcNAc changes, using the antibodies developed and characterized in Example 9. 5-20 µl of blood (cell or Plasma) proteins solubilized in RIPA buffer will be precipitated as described above using ice-cold 10% trichloroacetic acid/5% phosphotungstic acid (TCA/PTA) into wells of a 96 well filter plate (nitrocellulose or PVDF). Multiple 5-10 µl samples for each blood specimen will be precipitated, as required for each assay.

Each monoclonal antibody to one of 5 to 10 naked sites will be labeled with Cy3. Corresponding antibodies specific for the same O-GlcNAc-modified sites will be labeled with Cy5, and a panspecific monoclonal antibody to human hemoglobin will be labeled with Cy2. Preliminary studies will determine how much C2-tagged anti-Hb antibody to use. We will titrate it with unlabeled antibody so that its signal is about equal to the smallest readily quantifiable signal from an O-GlcNAc modified protein in normal blood samples, but such that the signal is still linearly dependent upon the amount of Hb present. Recent work has shown that by coupling the cyanin dyes antibodies via dextran linkers prevents dye quenching and increases the sensitivity of this approach by ~100-fold.

Five to ten (depending upon the number of antibodies produced, and the dynamic range of the O-GlcNAc response) standard mixtures of each antibody set will be prepared as stock solutions. Each of the five to ten stocks will contain Cy3-anti-peptide, Cy5-anti-O-GlcNAc-peptide, and the appropriate amount of Cy2-anti-Hb antibody. Also, in initial studies the linearity of the signals and constancy of fluorescent ratios from each antibody in terms of the amount of blood proteins added will be documented. In addition, controls will be performed in which the proteins will be deglycosylated using recombinant O-GlcNAcase prior to assay or increase their glycosylation using recombinant O-GlcNAc Transferase and UDP-GlcNAc in vitro prior to assay. Finally in this format, the specificity will be documented by examining the ability of naked and modified peptides to specifically compete for signals observed.

After transferring TCA/PTA precipitated blood proteins to 96 well plates, the samples will be washed 3× with 50% ethanol, and subsequently with PBS. Stock mixtures of labeled antibodies will then be added to each well, incubated for 1 h at 4° C. Five to ten wells will be used (~50 to 100 µA of blood total) for each sample. The ratios of Cy5/Cy3; Cy5/Cy2; Cy3/Cy2 fluorescence will be determined using a Molecular Devices SpectraMax M2 flourescent plate reader using SoftMax Pro software. Using synthetic peptides, O-GlcNAc peptides coupled to either KLH or BSA or both, standard curves will be established to document sensitivity, range, linearity, reproducibility and range of ratios that are detectable prior to extensive studies with blood samples. All analyses will be repeated several times to allow statistical significance to be determined.

EXAMPLE 13

Immobilized Antibodies and Differentially Labeled Antigens

This approach is based upon recent developments in antibody arrays, where sensitivities of detection have been reported to be as low as 1 ng/ml. However, the 'array' provided herein will have up to 3 duplicates of ~20 different monoclonal antibodies. Commercially available Protein-G or Protein A (Sigma; Pierce) coated plates will be used to directionally bind antibodies by their Fc portions. Three wells for each naked peptide antibody adjacent to three wells for each O-GlcNAc-peptide antibody will be used. Therefore, if there are ten anti-naked and ten anti-O-GlcNAc antibodies in these assay development tests, a single blood sample will require up to sixty separate wells. Six additional wells each will contain antibodies to proteins in serum (e.g., albumin) or blood cells (hemoglobin) to serve as a reference for mixing between normal and 'diabetic' samples.

As in well-known DNA microarray methods, the use of two-color mixed labeling allows a direct determination of ratios of specific antigens. Equal amounts blood samples from pooled (pooled from at-least ten normal individuals) "normal" blood and diabetic blood will be 'tagged'. Normal blood proteins will be labeled with Cy3-hydroxysuccinimide (NHS) esters (identical to the method used for the 'minimal' DIGE labeling). An equal amount of diabetic blood sample will be labeled with Cy5-hydroxysuccinimide (NHS) esters. Equal volumes will then be mixed and added to wells of the 96-well plates containing the antibodies. The plates will be washed several times with PBS or other buffers and read in a fluorescent plate reader. Average Cy5 or Cy3 fluorescence will be determined for each well and average ratios, and standard deviation generated for each O-GlcNAc site. Control wells (three each) will include a comparison of normal blood samples to itself and 'diabetic' blood sample to itself using the same labeling protocol. In addition controls in which the proteins are deglycosylated using recombinant O-GlcNAcase prior to assay or increase their glycosylation using recombinant O-GlcNAc Transferase and UDP-GlcNAc in vitro prior to assay. Finally in this format, the specificity will be documented by examining the ability of naked and modified peptides or KLH/BSA conjugates of the peptides to specifically compete for signals observed.

EXAMPLE 14

Dried Bloodspot Assays

These assays are routinely used to assay for hormones, and to screen newborns for inborn errors of metabolism. Benefits of bloodspot assays include speed and ease of collection, minimal invasiveness, microliter blood volume requirement and ease of transportation and storage of specimens before analyses. Blood collection filter paper cards (S&S 903) can be used. Blood (up to 50 µl) is spotted on filter cards and allowed to dry at room temperature overnight or 2 h at 45° C. The cards can then be stored in a sealed bag with dessicant at −20° C. for at least 2 months. Cards are brought to room temperature. 3-mm discs are punched from the cards using two punches on clean cards between each sample to minimize carry over.

Discs are placed into assay well, mixed with antibody for ELISA and chemiluminescence.

EXAMPLE 15

Dipstick Assays

After working out conditions and validating the assays in the 96 well format, the assay will be adapted to a simple 'dipstick' format, as has been done for detection of distinct malarial species in blood. The goal of this exercise it to validate that it is possible to use the antibodies to produce a robust, simple assay in which the strips can be stored for prolonged periods, and the assay can be performed by unskilled personnel. Strips of PVDF or nitrocellulose or glass slides coated with protein-G will be spotted (0.5 to 1 µl) with antibody pairs of antibodies specific for unmodified and O-GlcNAc modified sites, respectively. Strips/Plates will be blocked with BSA or casein. Blood proteins will be labeled with cyanine dyes or Alexa dyes as described above and diluted to the appropriate concentration, as determined by the microtiter assays (above). Labeled antigens will then be bound by "dipping" the strips/plates into the diluted/labeled samples. Strips will be washed by dipping into PBS dried and read using a fluorescent plate reader. Data analyses will be done sufficiently to determine standard deviations, reproducibility, dynamic ranges and sensitivities. Controls exactly as described above for plate assays will be performed.

EXAMPLE 16

O-GlcNAcase as a Marker of Pre-Diabetes

The present findings clearly support that the levels of O-GlcNAcase may be highly useful as markers to detect the early stages of diabetes. A more sensitive and quantitative assay for O-GlcNAcase is needed, in addition to the western blotting. ELISA assays have proven difficult in erythrocytes, due to interference, most likely from heme contamination.

mRNA O-GlcNAcase will be quantified by RT-PCR. A sensitive capillary electrophoresis assay using tagged glycopeptides and laser fluorescence detection will be used to accurately quantify the enzyme activity in the patient samples. Fluorescent-based ELISA assays will be used to detect O-GlcNAcase protein.

As an alternative, a double-label fluorescence ratio method in which the antibody to OGase is tagged with a Cy5 dye and antibody to actin is tagged with a Cy3 dye will be used. This will provide a ratio with a larger dynamic range than current Western blotting.

All of these methods have a larger dynamic range and sensitivity than the current data, and will allow statistics to be employed using many assays, since they require only small amounts of sample and are rapid.

Although the invention has been described with reference to the above example, it will be understood that modifications and variations are encompassed within the spirit and scope of the invention. Accordingly, the invention is limited only by the following claims.

What is claimed is:

1. A method of diagnosing a subject as having or at risk of having pre-diabetes or diabetes, comprising:
   a) obtaining a blood sample from the subject;
   b) isolating erythrocytes having erythrocyte peptides from the blood sample, the erythrocyte peptides comprising at least one of the amino acid sequences selected from SEQ ID NOs: 1, 2, 3, 5, 7, 8, 15-17, 24, 26, 28-32 or 37, and optionally isolating the erythrocyte peptides having the selected amino acid sequences from the isolated erythrocytes;
   c) performing an immunoassay to detect a level of O-linked N-acetyl-glucosamine (O-GlcNAc) modification of an amino acid residue within the amino acid sequence of at least one of the selected amino acid sequences of the erythrocyte peptides, the immunoassay comprising contacting the isolated erythrocytes or erythrocyte peptides with at least one first antibody that specifically binds to O-GlcNAc present on the amino acid residue of the at least one selected amino acid sequence of the erythrocyte peptides, wherein the at least one first antibody does not specifically bind other O-GlcNAc-modified peptides not having the at least one selected amino acid sequence, and with at least one second antibody that specifically binds the amino acid residue of the at least one selected amino acid sequence in a non-O-linked glycosylated state and detecting the first and second antibody bound to the O-GlcNAc-modified and non-O-glycosylated amino acid residue, respectively, of the at least one selected amino acid sequence; and
   d) calculating a ratio of bound first antibody to bound second antibody and comparing the ratio to that of a corresponding normal sample, wherein if the ratio is different from the ratio of the corresponding normal sample a diagnosis of pre-diabetes or diabetes, or an increased risk therefore, is indicated for the subject.

2. The method of claim 1, wherein the first or second antibody is detectably labeled.

3. The method of claim 1, wherein the second antibody is a monoclonal antibody.

4. The method of claim 1, wherein the second antibody is detectably labeled.

5. A method of monitoring a therapeutic regimen for treating a subject having or at risk of having hyperglycemia, comprising:
   a) obtaining a blood sample from the subject;
   b) isolating erythrocytes having erythrocyte peptides from the blood sample, the erythrocyte peptides comprising at least one of the amino acid sequences selected from SEQ ID Nos: 1, 2, 3, 5, 7, 8, 15-17, 24, 26, 28-32 or 37, and optionally isolating the erythrocyte peptides having the selected amino acid sequences from the isolated erythrocytes;
   c) performing an immunoassay to detect a level of O-linked N-acetyl-glucosamine (O-GlcNAc) modification of an amino acid residue within the amino acid sequence of at least one of the selected amino acid sequences of the erythrocyte peptides, the immunoassay comprising contacting the isolated erythrocytes or erythrocyte proteins with at least one first antibody that specifically binds O-GlcNAc present on the amino acid residue of the at least one selected amino acid sequence of the erythrocyte peptides, wherein the at least one first antibody does not specifically bind other O-GlcNAc-modified peptides not having the at least one selected amino acid sequence, and with at least one second antibody that specifically binds the amino acid residue of the at least one selected amino acid sequence in a non-O-linked glycosylated state and detecting the first and second antibody bound to the O-GlcNAc-modified and non-O-glycosylated amino acid residue, respectively, of the at least one selected amino acid sequence;
   d) calculating a ratio of bound first antibody to bound second antibody and comparing the ratio to that of a corresponding normal sample; and
   e) administering insulin to the subject where the ratio is different from the ratio of the corresponding normal sample.

6. A kit comprising:
   a) first container containing a first antibody that specifically binds O-linked N-acetyl-glucosamine (O-G1cNAc) present on an amino acid residue of a peptide, wherein the peptide is selected from SEQ ID NOs: 1-40 and wherein the first antibody does not specifically bind other O-G1cNAc-modified peptides not having the amino acid sequence of the selected peptide, and a second antibody that specifically binds the amino acid residue of the selected peptide in a non-O-linked glycosylated state; and
   b) a second container containing a first detectably labeled reporter.

7. The kit of claim 6, further comprising a second detectably labeled reporter.

8. A method of diagnosing a subject as having or at risk of having pre-diabetes or diabetes, comprising:
   a) obtaining a blood sample from the subject;
   b) isolating erythrocytes from the blood sample; and
   c) performing an immunoassay to detect an increased level of β-N-acetylglucosaminidase (O-GlcNAcase) in the erythrocytes as compared to the level of O-GlcNAcase in a corresponding normal sample, wherein the immunoassay comprises contacting the erythrocytes with an antibody that binds O-G1cNAcase and detecting the bound antibody, wherein detection of the bound antibody is indicative of the level of O-G1cNAcase in the erythrocytes, and wherein an increased level of O-G1cNAcase as compared to that of the normal sample is indicative of the subject as having or at risk of having pre-diabetes or diabetes, thereby diagnosing the subject.

9. The method of claim 8, wherein the antibody is a monoclonal antibody.

10. The method of claim 8, wherein the antibody is detectably labeled.

* * * * *

```
                        SEQUENCE LISTING

<160> NUMBER OF SEQ ID NOS: 43

<210> SEQ ID NO 1
<211> LENGTH: 18
<212> TYPE: PRT
<213> ORGANISM: Homo sapiens

<400> SEQUENCE: 1

Lys Leu Ser Thr Pro Pro Pro Leu Ala Glu Glu Glu Gly Leu Ala Ser
1               5                   10                  15

Arg Ile

<210> SEQ ID NO 2
<211> LENGTH: 16
<212> TYPE: PRT
<213> ORGANISM: Homo sapiens

<400> SEQUENCE: 2

Lys Val Val Thr Asp Glu Thr Ser Phe Val Leu Val Ser Asp Lys His
1               5                   10                  15

<210> SEQ ID NO 3
<211> LENGTH: 12
<212> TYPE: PRT
<213> ORGANISM: Homo sapiens

<400> SEQUENCE: 3

Arg Glu Pro Gly Gly Ser Leu Ser Phe Leu Arg Lys
1               5                   10

<210> SEQ ID NO 4
<211> LENGTH: 17
<212> TYPE: PRT
```

```
<213> ORGANISM: Homo sapiens

<400> SEQUENCE: 4

Arg Ile Ser Glu Ile Leu Leu Asp His Gly Ala Pro Ile Gln Ala Lys
1               5                   10                  15

Thr

<210> SEQ ID NO 5
<211> LENGTH: 13
<212> TYPE: PRT
<213> ORGANISM: Homo sapiens

<400> SEQUENCE: 5

Arg Asp Ser Gly Glu Gly Asp Thr Thr Ser Leu Arg Leu
1               5                   10

<210> SEQ ID NO 6
<211> LENGTH: 12
<212> TYPE: PRT
<213> ORGANISM: Homo sapiens

<400> SEQUENCE: 6

Arg Glu Ala Asp Ala Ala Thr Ser Phe Leu Arg Ala
1               5                   10

<210> SEQ ID NO 7
<211> LENGTH: 13
<212> TYPE: PRT
<213> ORGANISM: Homo sapiens

<400> SEQUENCE: 7

Lys Asp Ser Tyr Val Gly Asp Glu Ala Gln Ser Lys Arg
1               5                   10

<210> SEQ ID NO 8
<211> LENGTH: 13
<212> TYPE: PRT
<213> ORGANISM: Homo sapiens

<400> SEQUENCE: 8

Lys Glu Ile Thr Ala Leu Ala Pro Ser Thr Met Lys Ile
1               5                   10

<210> SEQ ID NO 9
<211> LENGTH: 15
<212> TYPE: PRT
<213> ORGANISM: Homo sapiens

<400> SEQUENCE: 9

Lys Gln Glu Tyr Asp Glu Ser Gly Pro Ser Ile Val His Arg Lys
1               5                   10                  15

<210> SEQ ID NO 10
<211> LENGTH: 10
<212> TYPE: PRT
<213> ORGANISM: Homo sapiens

<400> SEQUENCE: 10

Arg Val Ser Ser Gln Asp Tyr Gly Arg Asp
1               5                   10

<210> SEQ ID NO 11
<211> LENGTH: 14
<212> TYPE: PRT
```

```
<213> ORGANISM: Homo sapiens

<400> SEQUENCE: 11

Arg Val Ile Leu Glu Asn Ile Ala Ser His Glu Pro Arg Ile
1               5                   10

<210> SEQ ID NO 12
<211> LENGTH: 16
<212> TYPE: PRT
<213> ORGANISM: Homo sapiens

<400> SEQUENCE: 12

Arg Leu Ser Glu Ser His Pro Asp Ala Thr Glu Asp Leu Gln Arg Gln
1               5                   10                  15

<210> SEQ ID NO 13
<211> LENGTH: 17
<212> TYPE: PRT
<213> ORGANISM: Homo sapiens

<400> SEQUENCE: 13

Arg Gly Ala Leu Gln Asn Ile Ile Pro Ala Ser Thr Gly Ala Ala Lys
1               5                   10                  15

Ala

<210> SEQ ID NO 14
<211> LENGTH: 10
<212> TYPE: PRT
<213> ORGANISM: Homo sapiens

<400> SEQUENCE: 14

Arg Val Ser Thr Glu Val Asp Ala Arg Leu
1               5                   10

<210> SEQ ID NO 15
<211> LENGTH: 12
<212> TYPE: PRT
<213> ORGANISM: Homo sapiens

<400> SEQUENCE: 15

Lys Ala Thr Ala Val Val Asp Gly Ala Phe Lys Glu
1               5                   10

<210> SEQ ID NO 16
<211> LENGTH: 11
<212> TYPE: PRT
<213> ORGANISM: Homo sapiens

<400> SEQUENCE: 16

Arg Leu Ser Glu Asp Tyr Gly Val Leu Lys Thr
1               5                   10

<210> SEQ ID NO 17
<211> LENGTH: 15
<212> TYPE: PRT
<213> ORGANISM: Homo sapiens

<400> SEQUENCE: 17

Arg Thr Gln Ala Thr Phe Pro Ile Ser Ser Leu Gly Asp Arg Lys
1               5                   10                  15

<210> SEQ ID NO 18
<211> LENGTH: 9
<212> TYPE: PRT
```

```
<213> ORGANISM: Homo sapiens

<400> SEQUENCE: 18

Arg Gly Ser Val Pro Ile Leu Arg Gln
1               5

<210> SEQ ID NO 19
<211> LENGTH: 11
<212> TYPE: PRT
<213> ORGANISM: Homo sapiens

<400> SEQUENCE: 19

Arg Val Ser Phe Glu Leu Phe Ala Asp Lys Val
1               5                   10

<210> SEQ ID NO 20
<211> LENGTH: 12
<212> TYPE: PRT
<213> ORGANISM: Homo sapiens

<400> SEQUENCE: 20

Arg Thr Phe Asp Glu Ile Ala Ser Gly Phe Arg Gln
1               5                   10

<210> SEQ ID NO 21
<211> LENGTH: 14
<212> TYPE: PRT
<213> ORGANISM: Homo sapiens

<400> SEQUENCE: 21

Lys Thr Ile Leu Ile Ser Ala His Gly Asn Ser Ser Arg Ala
1               5                   10

<210> SEQ ID NO 22
<211> LENGTH: 12
<212> TYPE: PRT
<213> ORGANISM: Homo sapiens

<400> SEQUENCE: 22

Arg Asp Val Ser Ser Val Glu Leu Leu Met Lys Tyr
1               5                   10

<210> SEQ ID NO 23
<211> LENGTH: 12
<212> TYPE: PRT
<213> ORGANISM: Homo sapiens

<400> SEQUENCE: 23

Lys Asp Leu Thr Ser Val Leu Ile Leu Gln Arg Lys
1               5                   10

<210> SEQ ID NO 24
<211> LENGTH: 15
<212> TYPE: PRT
<213> ORGANISM: Homo sapiens

<400> SEQUENCE: 24

Lys Leu Leu Thr Ser Gln Asp Val Ser Tyr Asp Glu Ala Arg Asn
1               5                   10                  15

<210> SEQ ID NO 25
<211> LENGTH: 19
<212> TYPE: PRT
<213> ORGANISM: Homo sapiens
```

```
<400> SEQUENCE: 25

Arg Ala Gln Gly Leu Leu Ser Ala Gly His Pro Glu Gly Glu Gln Ile
1               5                   10                  15

Ile Arg Leu

<210> SEQ ID NO 26
<211> LENGTH: 10
<212> TYPE: PRT
<213> ORGANISM: Homo sapiens

<400> SEQUENCE: 26

Lys Asn Gly Pro Glu Gln Trp Ser Lys Leu
1               5                   10

<210> SEQ ID NO 27
<211> LENGTH: 12
<212> TYPE: PRT
<213> ORGANISM: Homo sapiens

<400> SEQUENCE: 27

Lys Tyr Ser Ser Leu Ala Glu Ala Ala Ser Lys Ala
1               5                   10

<210> SEQ ID NO 28
<211> LENGTH: 11
<212> TYPE: PRT
<213> ORGANISM: Homo sapiens

<400> SEQUENCE: 28

Lys Gly Gly Pro Phe Ser Asp Ser Tyr Arg Leu
1               5                   10

<210> SEQ ID NO 29
<211> LENGTH: 16
<212> TYPE: PRT
<213> ORGANISM: Homo sapiens

<400> SEQUENCE: 29

Lys Glu Ser Ile Ser Val Ser Ser Glu Gln Leu Ala Gln Phe Arg Ser
1               5                   10                  15

<210> SEQ ID NO 30
<211> LENGTH: 20
<212> TYPE: PRT
<213> ORGANISM: Homo sapiens

<400> SEQUENCE: 30

Lys His Asp Thr Ser Leu Lys Pro Ile Ser Val Ser Tyr Asn Pro Ala
1               5                   10                  15

Thr Ala Lys Glu
            20

<210> SEQ ID NO 31
<211> LENGTH: 21
<212> TYPE: PRT
<213> ORGANISM: Homo sapiens

<400> SEQUENCE: 31

Arg Phe Phe Glu Ser Phe Gly Asp Leu Ser Thr Pro Asp Ala Val Met
1               5                   10                  15

Gly Asn Pro Lys Val
            20
```

<210> SEQ ID NO 32
<211> LENGTH: 18
<212> TYPE: PRT
<213> ORGANISM: Homo sapiens

<400> SEQUENCE: 32

Lys Val Leu Gly Ala Phe Ser Asp Gly Leu Ala His Leu Asp Asn Leu
1               5                   10                  15

Lys Gly

<210> SEQ ID NO 33
<211> LENGTH: 15
<212> TYPE: PRT
<213> ORGANISM: Homo sapiens

<400> SEQUENCE: 33

Lys Gly Thr Phe Ala Thr Leu Ser Glu Leu His Cys Asp Lys Leu
1               5                   10                  15

<210> SEQ ID NO 34
<211> LENGTH: 10
<212> TYPE: PRT
<213> ORGANISM: Homo sapiens

<400> SEQUENCE: 34

Lys Leu Ser Val Pro Asp Gly Phe Lys Val
1               5                   10

<210> SEQ ID NO 35
<211> LENGTH: 10
<212> TYPE: PRT
<213> ORGANISM: Homo sapiens

<400> SEQUENCE: 35

Lys Asn Ser Ser Tyr Phe Pro Gly Lys Leu
1               5                   10

<210> SEQ ID NO 36
<211> LENGTH: 11
<212> TYPE: PRT
<213> ORGANISM: Homo sapiens

<400> SEQUENCE: 36

Arg Ala Ala Ala Thr Leu Met Ser Glu Arg Val
1               5                   10

<210> SEQ ID NO 37
<211> LENGTH: 16
<212> TYPE: PRT
<213> ORGANISM: Homo sapiens

<400> SEQUENCE: 37

Lys Ala Ser Thr Pro Gly Ala Ala Ala Gln Ile Gln Glu Val Lys Glu
1               5                   10                  15

<210> SEQ ID NO 38
<211> LENGTH: 16
<212> TYPE: PRT
<213> ORGANISM: Homo sapiens

<400> SEQUENCE: 38

Lys Ile Pro Pro Asp Ser Glu Ala Thr Leu Val Leu Val Gly Arg Ala
1               5                   10                  15

```
<210> SEQ ID NO 39
<211> LENGTH: 16
<212> TYPE: PRT
<213> ORGANISM: Homo sapiens

<400> SEQUENCE: 39

Arg Tyr Gln Ser Ser Pro Ala Lys Pro Asp Ser Ser Phe Tyr Lys Gly
1               5                   10                  15

<210> SEQ ID NO 40
<211> LENGTH: 13
<212> TYPE: PRT
<213> ORGANISM: Homo sapiens

<400> SEQUENCE: 40

Lys Leu Ser Ile Leu Tyr Pro Ala Thr Thr Gly Arg Asn
1               5                   10

<210> SEQ ID NO 41
<211> LENGTH: 12
<212> TYPE: PRT
<213> ORGANISM: Homo sapiens

<400> SEQUENCE: 41

Pro Ser Val Pro Val Ser Gly Ser Ala Pro Gly Arg
1               5                   10

<210> SEQ ID NO 42
<211> LENGTH: 11
<212> TYPE: PRT
<213> ORGANISM: Homo sapiens

<400> SEQUENCE: 42

Lys His Phe Pro Gln Phe Ser Tyr Ser Ala Ser
1               5                   10

<210> SEQ ID NO 43
<211> LENGTH: 4
<212> TYPE: PRT
<213> ORGANISM: Artificial Sequence
<220> FEATURE:
<223> OTHER INFORMATION: Consensus sequence

<400> SEQUENCE: 43

Pro Glu Ser Thr
1
```